US009778112B2

(12) United States Patent
Pate et al.

(10) Patent No.: US 9,778,112 B2
(45) Date of Patent: Oct. 3, 2017

(54) SEGMENTED CHIRPED-PULSE FOURIER TRANSFORM SPECTROSCOPY

(71) Applicant: University of Virginia Patent Foundation, Charlottesville, VA (US)

(72) Inventors: Brooks Hart Pate, Charlottesville, VA (US); Justin L. Neill, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 15/338,851

(22) Filed: Oct. 31, 2016

(65) Prior Publication Data

US 2017/0176256 A1 Jun. 22, 2017

Related U.S. Application Data

(63) Continuation of application No. 14/494,315, filed on Sep. 23, 2014, now Pat. No. 9,482,577, which is a (Continued)

(51) Int. Cl.
*G01J 3/30* (2006.01)
*G01J 3/443* (2006.01)
(Continued)

(52) U.S. Cl.
CPC ............ *G01J 3/443* (2013.01); *G01J 3/2889* (2013.01); *G01J 3/4338* (2013.01); *G01N 21/3586* (2013.01); *G01N 2021/3595* (2013.01)

(58) Field of Classification Search
CPC .... G01J 3/443; G01J 3/28; G01J 3/30; G01N 21/62; G01N 21/67; G01N 21/69; G01N 21/3103

See application file for complete search history.

(56) References Cited

U.S. PATENT DOCUMENTS 3,909,705 A 9/1975 Tschopp
4,464,570 A 8/1984 Allemann et al.
(Continued)

FOREIGN PATENT DOCUMENTS

CN 101512286 A 8/2009
CN 103583003 A 2/2014
(Continued)

OTHER PUBLICATIONS

"U.S. Appl. No. 13/704,483, Notice of Allowance dated Feb. 3, 2015", 10 pgs.
(Continued)

*Primary Examiner* — Abdullahi Nur
(74) *Attorney, Agent, or Firm* — Schwegman Lundberg & Woessner P.A.

(57) ABSTRACT

An emission can be obtained from a sample in response to excitation using a specified range of excitation frequencies. Such excitation can include generating a specified chirped waveform and a specified downconversion local oscillator (LO) frequency using a digital-to-analog converter (DAC), upconverting the chirped waveform via mixing the chirped waveform with a specified upconversion LO frequency, frequency multiplying the upconverted chirped waveform to provide a chirped excitation signal for exciting the sample, receiving an emission from sample, the emission elicited at least in part by the chirped excitation signal, and downconverting the received emission via mixing the received emission with a signal based on the specified downconversion LO signal to provide a downconverted emission signal within the bandwidth of an analog-to-digital converter (ADC). The specified chirped waveform can include a first chirped waveform during a first duration, and a second chirped waveform during a second duration.

21 Claims, 14 Drawing Sheets

Related U.S. Application Data continuation of application No. 13/912,548, filed on Jun. 7, 2013, now Pat. No. 8,873,043, which is a continuation-in-part of application No. PCT/US2012/029430, filed on Mar. 16, 2012.

(60) Provisional application No. 61/656,665, filed on Jun. 7, 2012, provisional application No. 61/454,223, filed on Mar. 18, 2011.

(51) Int. Cl.
  *G01J 3/28* (2006.01)
  *G01J 3/433* (2006.01)
  *G01N 21/3586* (2014.01)
  *G01N 21/35* (2014.01)

(56) References Cited

U.S. PATENT DOCUMENTS

| | | | |
|---|---|---|---|
| 4,967,160 | A | 10/1990 | Quievy et al. |
| 5,047,636 | A | 9/1991 | Farrar et al. |
| 5,508,661 | A | 4/1996 | Keane et al. |
| 8,300,228 | B2 | 10/2012 | Marks et al. |
| 8,748,822 | B1 | 6/2014 | Gerecht et al. |
| 8,873,043 | B2 | 10/2014 | Pate et al. |
| 9,046,462 | B2 | 6/2015 | Pate et al. |
| 9,442,079 | B2 | 9/2016 | Pate et al. |
| 9,482,577 | B2 | 11/2016 | Pate et al. |
| 2004/0007666 | A1 | 1/2004 | Griffey et al. |
| 2005/0058218 | A1 | 3/2005 | Jenkins |
| 2005/0168735 | A1 | 8/2005 | Boppart et al. |
| 2006/0049981 | A1 | 3/2006 | Merkel et al. |
| 2007/0223936 | A1 | 9/2007 | Babbitt et al. |
| 2008/0224908 | A1 | 9/2008 | Li et al. |
| 2008/0285606 | A1 | 11/2008 | Kippenberg et al. |
| 2009/0073432 | A1* | 3/2009 | Jalali ............ G01J 3/10 356/301 |
| 2009/0161092 | A1 | 6/2009 | Zanni et al. |
| 2010/0046003 | A1 | 2/2010 | Le Floch et al. |
| 2010/0290025 | A1 | 11/2010 | Parker |
| 2013/0154611 | A1 | 6/2013 | Pate et al. |
| 2013/0265573 | A1 | 10/2013 | Pate et al. |
| 2015/0253261 | A1 | 9/2015 | Pate et al. |
| 2015/0260575 | A1 | 9/2015 | Pate et al. |
| 2016/0131600 | A1 | 5/2016 | Pate et al. |
| 2017/0089831 | A1 | 3/2017 | Pate et al. |

FOREIGN PATENT DOCUMENTS

| | | |
|---|---|---|
| CN | 103583003 B | 11/2016 |
| JP | 2016521859 A | 7/2016 |
| TW | 201510504 A | 3/2015 |
| WO | WO-2011160013 A1 | 12/2011 |
| WO | WO-2012129089 A1 | 9/2012 |
| WO | WO-2014201230 A1 | 12/2014 |

OTHER PUBLICATIONS

"U.S. Appl. No. 13/704,483, Notice of Allowance dated Oct. 9, 2014", 11 pgs.
"U.S. Appl. No. 13/704,483, Preliminary Amendment filed Dec. 14, 2012", 8 pgs.
"U.S. Appl. No. 13/912,548, Notice of Allowance dated Mar. 18, 2014", 12 pgs
"U.S. Appl. No. 13/912,548, Notice of Allowance dated Jul. 1, 2014", 9 pgs.
"U.S. Appl. No. 14/494,315, Final Office Action dated Dec. 31, 2015", 9 pgs.
"U.S. Appl. No. 14/494,315, Non Final Office Action dated Jul. 8, 2015", 6 pgs.
"U.S. Appl. No. 14/494,315, Notice of Allowance dated Jun. 29, 2016", 9 pgs.
"U.S. Appl. No. 14/494,315, Response filed May 3, 2016 to Final Office Action dated Dec. 31, 2015", 8 pgs.
"U.S. Appl. No. 14/494,315, Response filed Dec. 7, 2015 to Non Final Office Action dated Jul. 8, 2015", 9 pgs.
"U.S. Appl. No. 14/718,624, Final Office Action dated Dec. 30, 2015", 8 pgs.
"U.S. Appl. No. 14/718,624, Non Final Office Action dated Jul. 16, 2015", 6 pgs
"U.S. Appl. No. 14/718,624, Notice of Allowance dated Apr. 4, 2016", 12 pgs.
"U.S. Appl. No. 14/718,624, Notice of Allowance dated May 10, 2016", 6 pgs.
"U.S. Appl. No. 14/718,624, Response filed Feb. 29, 2016 to Final Office Action dated Dec. 30, 2015", 11 pgs.
"U.S. Appl. No. 14/718,624, Response filed Oct. 16, 2015 to Non Final Office Action dated Jul. 16, 2015", 7 pgs.
"U.S. Appl. No. 14/898,077, Examiner Summary dated May 12, 2017", 1 pg.
"U.S. Appl. No. 15/255,036, Non Final Office Action dated Jan. 12, 2017", 9 pgs.
"U.S. Appl. No. 15/255,036, Preliminary Amendment filed Dec. 15, 2016", 7 pgs.
"Chinese Application Serial No. 201280023629.7, Office Action dated Feb. 1, 2016", 16 pgs.
"Chinese Application Serial No. 201280023629.7, Voluntary Amendment dated Mar. 20, 2014", in Chinese Only, 10 pgs
"European Application Serial No. 11796503.8, Communication pursuant to Article 94(3) EPC dated Aug. 3, 2016", 5 pgs.
"European Application Serial No. 11796503.8, Extended European Search Report dated Sep. 24, 2015", 8 pgs.
"European Application Serial No. 11796503.8, Response filed Apr. 25, 2016", 12 pgs.
"European Application Serial No. 11796503.8, Response filed Dec. 12, 2016 to Communication pursuant to Article 94(3) EPC dated Aug. 3, 2016", 11 pgs.
"European Application Serial No. 12761002.0, Extended European Search Report dated Aug. 14, 2014", 6 pgs.
"European Application Serial No. 12761002.0, Response filed May 6, 2014", 15 pgs.
"European Application Serial No. 12761002.0, Response filed Aug. 18, 2015", 21 pgs.
"European Application Serial No. 14811595.9, Response to Communication pursuant to Rules 161(2) and 162 EPC dated Aug. 17, 2016", 20 pgs.
"European Application Serial No. 14811595.9, Supplemental European Search Report dated Feb. 3 ,2017", 6 pgs.
"International Application Serial No. PCT/US2011/040876, VVritten Opinion dated Oct. 5, 2011", 9 pgs.
"International Application Serial No. PCT/US2011/040876, International Preliminary Report on Patentability dated Jan. 3, 2013", 11 pgs.
"International Application Serial No. PCT/US2011/040876, International Search Report dated Oct. 5, 2011", 2 pgs.
"International Application Serial No. PCT/US2012/029430, International Preliminary Report on Patentability dated Oct. 3, 2013", 8 pgs.
"International Application Serial No. PCT/US2012/029430, International Search Report dated Jul. 11, 2012", 4 pgs.
"International Application Serial No. PCT/US2012/029430, Written Opinion dated Jul. 11, 2012", 6 pgs.
"International Application Serial No. PCT/US2014/042094, International Preliminary Report on Patentability dated Dec. 23, 2015", 7 pgs.
"International Application Serial No, PCT/US2014/042094, International Search Report dated Nov. 20, 2014", 4 pgs.
"International Application Serial No. PCT/US2014/042094, Invitation to Pay Additional Fees and Partial Search Report dated Sep. 9, 2014", 2 pgs.
"International Application Serial No. PCT/US2014/042094, Written Opinion dated Nove. 20, 2014", 5 pgs.
"Tektronix AWG710B", Anonymous, (Nov. 1, 2002)

(56) References Cited

OTHER PUBLICATIONS

Balle, T.J, et al., "Fabry-Perot cavity pulsed Fourier transform microwave spectrometer with a pulsed nozzle particle source", Rev. Sci. Instrum., 52, (1981), 33-45.
Brown, G.G, et al., "A broadband Fourier transform microwave spectrometer based on chirped pulse excitation", Rev Sci Instrum., 79(5), American Institute of Physics, (May, 2008), 053103-1-053103-13.
Brown, Gordon, et al., "The rotational spectrum of epifluorohydrin measured by chirped-pulse Fourier transform microwave spectroscopy", Journal of Molecular Spectroscopy, 238(2), (Aug., 2006), 200-212.
Campbell, E.J, et al., "The theory of pulsed Fourier transform microwave spectroscopy carried out in a Fabry-Perot cavity: Static gas", J. Chem. Phys., 74, (1981), 813-828.
Coddington, Ian, et al., "Time-domain spectroscopy of molecular free-induction decay in the infrared", Optics Letters, vol. 35, No. 9, (2010), 1395-1397.
Crowe, T.W, et al., "Opening the terahertz window with integrated diode circuits", IEEE Journal of Solid-State Circuits, 40(10), (Oct., 2005), 2104-2110.
De Lucia, Frank C., "The submillimeter: A spectroscopist's view", Journal of Molecular Spectroscopy, 261(1), (May, 2010), 1-17.
Dian, B C, et al., "Measuring Picosecond Isomerization Kinetics via Broadband Microwave Spectroscopy", Science, vol. 320, No. 5878, (May 16, 2008), 924-928.
Dian, Brian C., et al., "Seeing Is Believing: An 11 GHz molecular beam rotational spectrum (7.5-18.5 GHz) with 100 kHz resolution in 15 us measurement time", International Symposium on Molecular Spectroscopy, (Jun. 20, 2005), 29 pgs.
Douglass, K.O, et al., "Progress towards chirped-pulse Fourier transform THz spectroscopy", 64th International Symposium on Molecular Spectroscopy, Columbus, OH, [Online]. Retrieved from the Internet: <URL: http://hdl.handle.net/1811/46369>, (Jun. 21-25, 2010.), 21 pgs.
Drouin, B.J, et al., "Application of cascaded frequency multiplication to molecular spectroscopy", Rev. Sci. Instrum., 76, (2005), 093113.
Ekkers, J., et al., "Pulsed microwave Fourier transform spectrometer", Rev. Sci. Instrum., 47, (1976), 448-454.
Finneran, I.A, et al., "A direct digital synthesis chirped pulse Fourier transform microwave spectrometer", Rev Sci Instrum., 84(8), (Aug., 2013), 083104.
Gerecht, E., et al., "Chirped-pulse terahertz spectroscopy for broadband trace gas sensing", Opt Express., 19(9), (Apr. 25, 2011), 8973-84.
Gerecht, Eyal, et al., "Chirped-Pulse Terahertz Spectroscopy for Broadband Tracegas Sensing", National Institute of Standards and Technology, Optical Technology Division, (Jun. 21, 2011), 24 pgs.
Gerecht, Eyal, et al., "Recent Progress in Chirped-Pulse Fourier Transform THz Spectroscopy", NIST, (Jun. 23, 2010), 20 pgs.
Gerecht, Eyal, et al., "Recent Progress in Chirped-Pulse Fourier Transform THz Spectroscopy (with embedded notes)", NIST, (Apr. 19, 2016), 40 pgs.
Green, Sheldon, "On the amount of information in rotational relaxation experiments with application to microwave transient T1 and T2 rates", J. Chem. Phys., 69, (1978), 4076-4082.
Hahn, E.L., "Spin Echos". Physical Review, 80(1), (1950), 580-594.
Harris, Brent, et al., "Segmented Chirped Pulse Fourier Transform (CP-FT) Millimeter Spectroscopy: Identification of Volatiles by Pure Rotation", Eastern Analytical Symposium & Exposition 2012, (2012), 1 pg.
Hoke, W.E, et al., "The measurement and interpretation of T1 and T2 in the inversion doublets of 15NH3 and the rotational transitions in OCS", J. Chem. Phys., 64, (1976), 5276-5282.
Kuyanov-Prozument, K., et al., "Direct Observation of Rydberg—Rydberg Transitions in Calcium Atoms", International Symposium on Molecular Spectroscopy, (Jun. 22, 2010), 20 pgs.

Lesarri, Alberto, et al., "Interplay of Phenol and Isopropyl Isomerism in Propofol from Broadband Chirped-Pulse Microwave Spectroscopy", American Chemical Society, vol. 132, No. 38, (Sep. 7, 2010), 13417-13424.
Mata, Santiago, "A broadband Fourier-transform microwave spectrometer with laser ablation source: The rotational spectrum of nicotinic acid", Journal of Molecular Spectroscopy 280: 91-96, (2012), 91-96.
Matton, S., et al., "Terahertz spectroscopy applied to the measurement of strengths and self-broadening coefficients for high-J lines of OCS", Journal of Molecular Spectroscopy, 239(2), (Oct., 2006), 182-189.
Medvedev, I.R, et al., "Chemical analysis in the submillimetre spectral region with a compact solid state system", Analyst, 131(12), (Dec., 2006), 1299-307.
Medvedev, Ivan R, et al., "Submillimeter spectroscopy for chemical analysis with absolute specificity", Optics Letters, 35(10), (2010), 1533-1535.
Neese, C.F, et al., "Compact Submillimeter/Terahertz Gas Sensor With Efficient Gas Collection, Preconcentration, and ppt Sensitivity", IEEE Sensors Journal, 12(8), (Aug., 2012), 2565-2574.
Neill, Justin L., et al., "Next generation techniques in the high resolution spectroscopy of biologically relevant molecules", Phys. Chem. Chem, Phys.,13, (2011), 7253-7262.
Neill, Justin L., et al., "Rotational spectroscopy of iodobenzene and iodobenzene-neon with a direct digital 2-8 GHz chirped-pulse Fourier transform microwave spectrometer", Journal of Molecular Spectroscopy, (2011), 21-29.
Neill, Justin L, et al., "Segmented chirped-pulse Fourier transform submillimeter spectroscopy for broadband gas analysis", Optics Express, 21(17), (2013), 19743-19749.
Neill, Justin L., et al,, "Techniques for High-Bandwidth (> 30 GHz) Chirped-Pulse Millimeter/Submillimeter Spectroscopy", (Jun. 23, 2011), 22 pgs.
Ozawa, a, et al., "High Harmonic Frequency Combs for High Resolution Spectroscopy", Physical Review Letters, vol. 100, No. 25, (Jun. 1, 2008).
Park, Barratt G, et al., "Design and evaluation of a pulsed-jet chirped-pulse milimeter-wave spectrometer for the 70-102 GHz region", AIP The Journal of Chemical Physics 135, 024202, (2011), 1-10.
Park, G.B, et al., "Design and chemical application of chirped-pulse millimeter-wave spectroscopy", 64th International Symposium on Molecular Spectroscopy, Columbus, OH [Online]. Retrieved from the Internet: <URL: http://hdl.hande.net/1811/38114:>, (41 pgs), Jun. 22-26, 2009.
Park, G. Barratt, et al., "Design and evaluation of a pulsed-jet chirped-pulse millimeter-wave spectrometer for the 70-102 GHz region", AIP The Journal of Chemical Physics 135, 024202, (2011), 1-10.
Pate, B.H, "Chemistry. Taking the pulse of molecular rotational spectroscopy", Science, 333(6045), (Aug. 19, 2011), 947-8.
Petkie, D.T, et al., "A fast scan submillimeter spectroscopic technique", Rev. Sci. Instrum., 68, (1997), 1675-1683.
Prozument, Kirill, "Chirped-Pulse Millimeter-Wave Spectroscopy of Rydberg-Rydberg Transitions", American Physical Society, (2011), 5 pgs.
Shipman, Steven T., et al., "Design and performance of a direct digital chirped-pulse Fourier transform microwave (CP-FTMW) spectrometer operating from 2-8 GHz", International Symposium on Molecular Spectroscopy, (Jun. 18, 2008), 29 pgs.
Shipman, Steven, et al., "Waveguide Chirped-Pulse FTMW Spectroscopy", (Jun. 18, 2008), 29 pgs.
Smith, Albert A, et al., "A 140 GHz pulsed EPR/212 MHz NMR spectrometer for DNP studies", Journal of Magnetic Resonance 223, [Online]. Retrieved from the Internet: <http://wwwsciencedirect.comiscience/article/pii/S1090780712002509>, (Jul. 20, 2012), 170-179.
Spokas, J.J, et al., "Nuclear Relaxation in Aluminum", Phys. Rev., 113, (Mar. 15, 1959), 1462.

(56) References Cited

OTHER PUBLICATIONS

Steber, Amanda L, et al., "An arbitrary waveform generator based chirped pulse Fourier transform spectrometer operating from 260 to 295 GHz", Journal of Molecular Spectroscopy, 280, (3-10), Oct., 2012.
Twagirayezu, Sylvestre, "Vibrational Coupling Pathways in Methanol As Revealed by Coherence-Converted Population Transfer Fourier Transform Microwave Infrared Double-Resonance Spectroscopy", J. Phys. Chem. A, vol. 114, No. 25, (2010), 6818-6828.
Yi-Da, Hsieh, et a., "Terahertz Comb Spectroscopy Traceable to Microwave Frequency Standard", IEEE Transactions on Terahertz Science and Technology, IEEE, Piscataway, NJ, USA, XP011506303, ISSN: 2156-342X, (Apr. 29, 2013), 322-330.
Zaleski, Daniel P., et al., "A Ka-Band Chirped-Pulse Fourier Transform Microwave Spectrometer", International Symposium on Molecular Spectroscopy, (Jun. 22, 2010), 17 pgs.
Zaleski, Daniel, et al., "A Ka-band chirped-pulse Fourier transform microwave spectrometer", Article in Journal of Molecular Spectroscopy, (October 2012), 10 pgs.
"European Application No. 14811595.9, Extended European Search Report dated May 15, 2017", 9 pgs.

\* cited by examiner

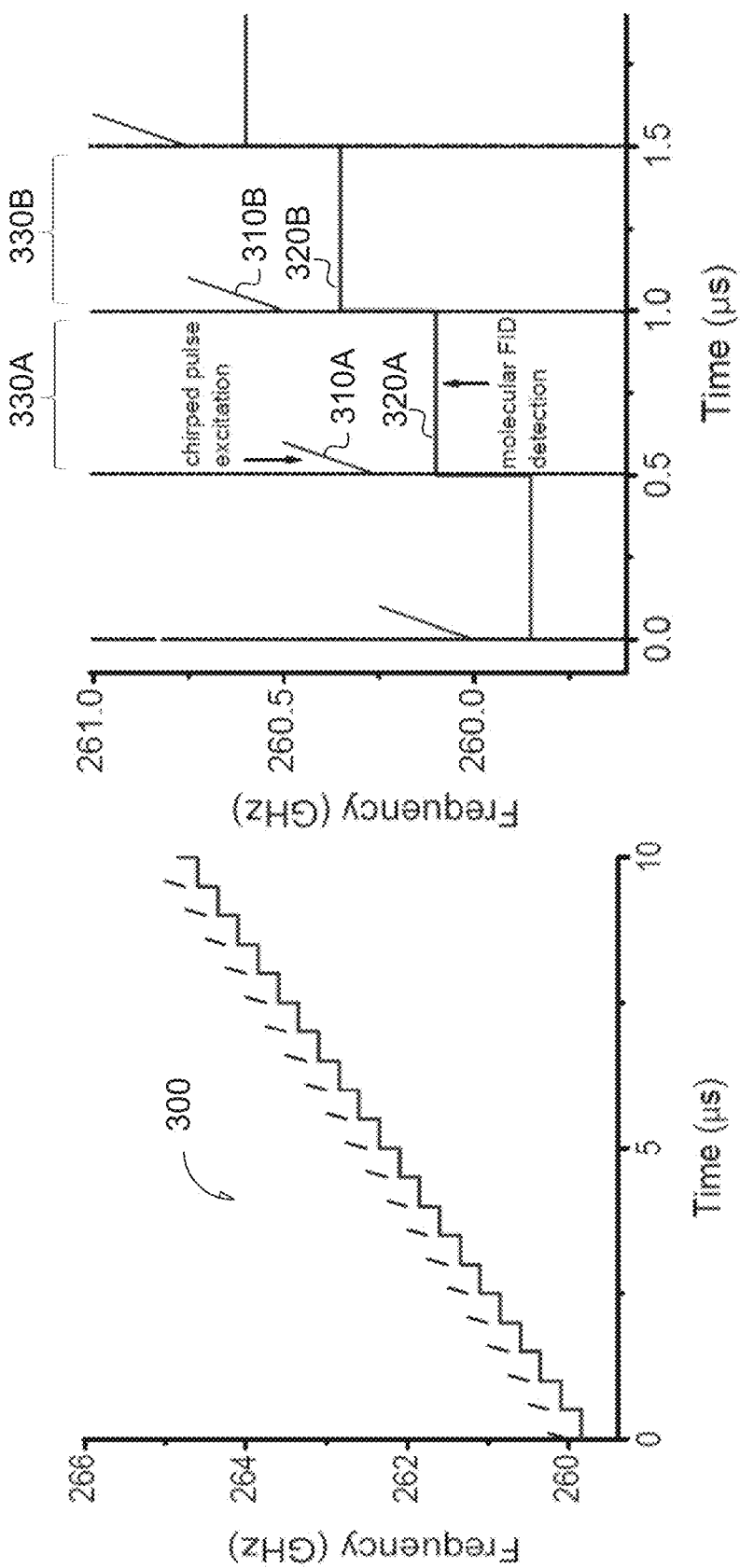

SEGMENTED CHIRPED-PULSE FOURIER TRANSFORM SPECTROSCOPY

CLAIM OF PRIORITY

This application is a continuation of U.S. patent application Ser. No. 14/494,315, filed on Sep. 23, 2014, which is a continuation of U.S. patent application Ser. No. 13/912,548, filed on Jun. 7, 2013, which is a continuation-in-part under 35 U.S.C. 111(a) of International Application No. PCT/US2012/029430, filed Mar. 16, 2012 and published on Sep. 27, 2012 as WO 2012/129089 A1, which claims benefit of priority under 35 U.S.C. 119(e) to U.S. Provisional Patent Application Ser. No. 61/454,223, filed on Mar. 18, 2011, the benefit of priority of each of which is claimed hereby, and each of which are incorporated by reference herein in its entirety. U.S. patent application Ser. No. 13/912,548 also claims the benefit of priority under 35 U.S.C. 119(e) to U.S. Provisional Patent Application Ser. No. 61/656,665, filed on Jun. 7, 2012, which is hereby incorporated by reference herein in its entirety.

STATEMENT REGARDING FEDERALLY-SPONSORED RESEARCH OR DEVELOPMENT

This invention was made with government support under Grant No. CHE-0847919 awarded by the National Science Foundation (NSF). The government has certain rights in the invention.

BACKGROUND

Spectroscopy, such as rotational spectroscopy, is a powerful structural tool in physical chemistry. For example, the relationship between a molecular structure and its rotational transition frequencies can be used for structure determination of gas phase samples. Other effects in the rotational motion of molecules, such as centrifugal distortion, hyperfine spectral structure from quadrupolar nuclei, or frequency shifts caused by tunneling motion, can be used to provide further characterization of the molecular structure and low frequency vibrational motions.

The millimeter (mm) wave or terahertz (THz) frequency region is a particularly useful region for chemical detection and characterization. For room temperature samples, this is the region where pure rotational spectra are most intense. All molecules with a permanent dipole moment have a pure rotational spectrum. Such a spectrum includes a large number of sharp transitions that can serve as a "fingerprint" of a molecular identity. For example, such transitions can be about 1 megahertz (MHz) in width at about 300 gigahertz (GHz) in a low-pressure gas cell. In one approach, the transition frequencies can be related back to the molecular identity, such as through fitting with a molecular Hamiltonian, which can explain measured transition frequencies and relative intensities in terms of calculable physical parameters. From the intensities of the transitions observed by millimeter- and sub-millimeter-wave spectroscopy, absolute molecular concentrations can be derived with high accuracy and selectivity.

Overview

In one approach, techniques for millimeter-wave spectroscopy involve measuring molecular transitions based on their absorption of radiation, using a synthesizer in the microwave frequency region, coupled to one or more frequency multipliers, as the radiation source. However, the slow scanning and switching speeds of such synthesizers preclude rapid detection of large bandwidths. For example, monitoring of complex chemical mixtures at desired video refresh rates is not possible using these techniques.

The present inventors have recognized, among other things, that a high-speed Digital-to-Analog converter (DAC), such as a high-speed Arbitrary Waveform Generator (AWG), can provide a frequency-agile source of energy including microwave frequencies, and can open new opportunities for the fast detection of millimeter wave spectra when included in a spectroscopy system instead of or in addition to generally-available synthesizers.

In an example, a DAC can create a high-bandwidth linear frequency sweep (e.g., a chirped pulse), which can be amplified such as to induce polarizations in a molecular sample at the frequencies of transitions within the bandwidth of the pulse. The sample then continues to emit radiation at the frequencies of the transitions, and such free induction decay (FID) emission signals can be digitized and Fourier transformed to yield a molecular spectrum. Such Chirped-Pulse Fourier Transform (CP-FT) techniques generally provide high sensitivity, dynamic range, and frequency accuracy in the detection of broadband molecular spectra. Due to the fast acquisition speed, short-lived species generated in sample cells, such as ions and radicals, can be characterized using CP-FT techniques. However, generally-available digitizer bandwidths are limited. Accordingly, the present inventors have also recognized that to collect higher-bandwidth spectra (e.g., spectra having a total bandwidth wider than an available digitizer bandwidth), a technique to reduce the required digitizer bandwidth is needed.

The present inventors have recognized, among other things, that a "segmented" CP-FT technique can be used, such as using the DAC to generate a chirped-pulse waveform, and using the DAC to generate one or more Local Oscillator (LO) frequencies. Such a segmented CP-FT method can reduce the bandwidth demanded for the digitizer by a "divide and conquer" approach that segments the total measurement bandwidth into a series of segments. For example, a bandwidth of a frequency multiplied chirped-pulse waveform can be specified at least in part based on an available digitizer bandwidth, and each segment can include a chirped pulse specified to excite the sample in such a manner that resulting emissions can be captured within the available digitizer bandwidth. A total bandwidth of interest to be measured can be wider than the digitizer bandwidth, and can be obtained via generating a series of respective chirped pulses and LO frequencies corresponding to each segment, obtaining emissions for each segment, then assembling an ensemble of respective estimated spectra corresponding to each segment to provide coverage of the total bandwidth of interest.

Using a DAC-based source, these segments can be measured in rapid succession to cover large frequency ranges. For example, received emissions can be downconverted using a heterodyne detection technique. Such heterodyne detection generally uses a high agility, phase-reproducible local oscillator (LO) source and this source can also be DAC-based, and is thus very rapidly tunable.

In an example, an emission can be obtained from a sample in response to excitation using a specified range of excitation frequencies. Such excitation can include generating a specified chirped waveform and a specified downconversion local oscillator (LO) frequency using a digital-to-analog converter (DAC), upconverting the chirped waveform via mixing the chirped waveform with a specified upconversion LO frequency, frequency multiplying the upconverted chirped waveform to provide a chirped excitation signal for exciting the sample, receiving an emission from sample, the emission elicited at least in part by the chirped excitation signal, and downconverting the received emission via mixing the received emission with a signal based on the specified downconversion LO signal to provide a downconverted emission signal within the bandwidth of an analog-to-digital converter (ADC). The specified chirped waveform can include a first chirped waveform during a first duration, and a second chirped waveform during a second duration.

The spectroscopy techniques and apparatus described herein can be generally applicable to both the microwave frequency region, and much higher frequencies (e.g., mm- or sub-millimeter wavelengths—which include frequencies in the terahertz (THz) region of the electromagnetic spectrum). For example, generally-available frequency multipliers can provide signals into the mm-region (or even shorter wavelengths), and have made possible the generation of phase-stable radiation with high frequency precision for high-sensitivity spectroscopy.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

FIG. 3A illustrates generally an illustrative example of a spectrogram representation of the DAC channel outputs, such as corresponding to a dual-channel example, and FIG. 3B illustrates generally a detailed view of a portion of FIG. 3A.

Figure 1:
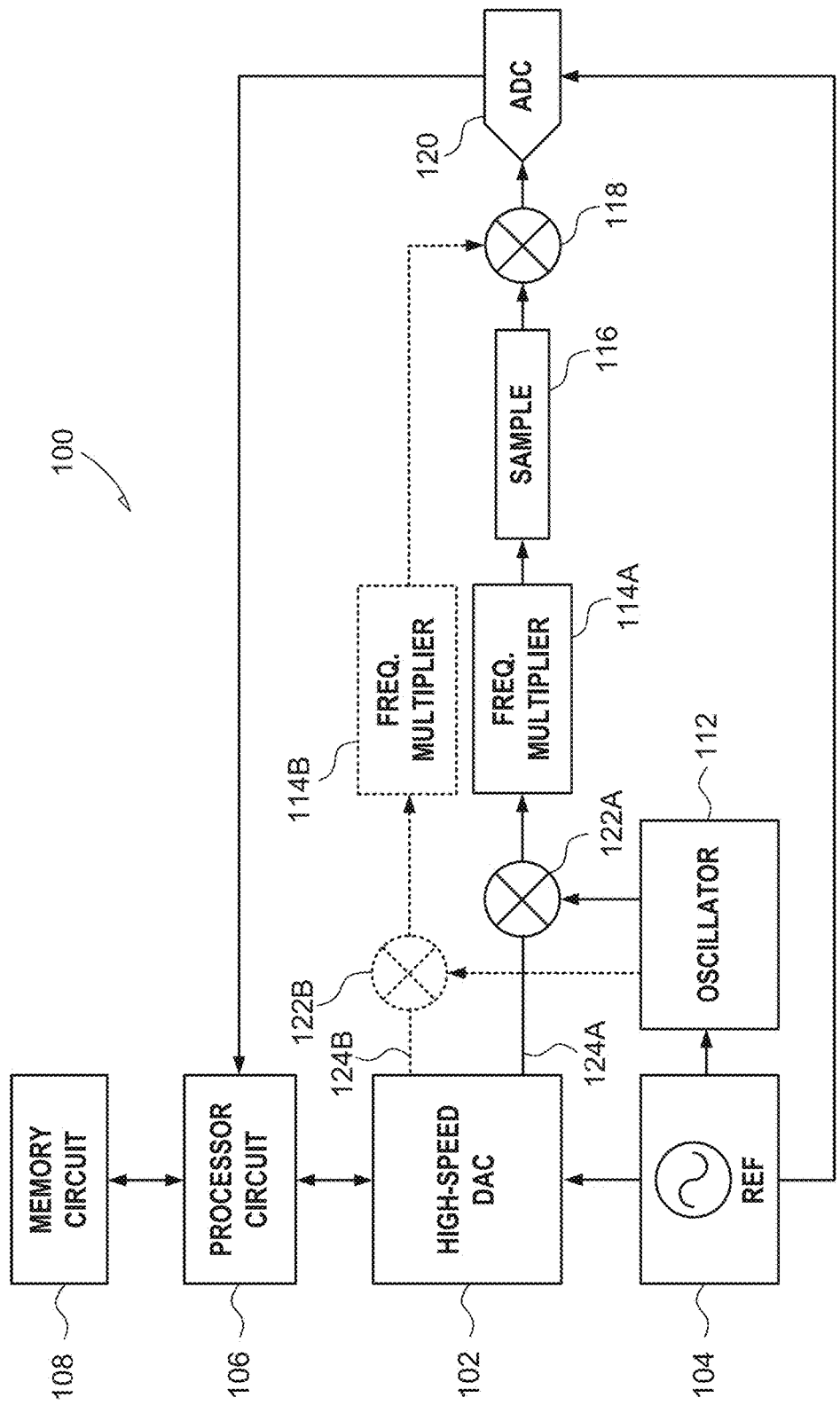
FIG. 1 illustrates generally an example of a system for generating a chirped-pulse excitation signal, and for obtaining emission from a sample in response to such excitation.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

FIG. 1 illustrates generally an example of a system 100, such as can be used for generating a chirped-pulse excitation signal, or for obtaining emission from a sample in response to such excitation. In an example, the system 100 can include at least one processor circuit 106, such as coupled to a memory circuit 108 (or one or more other storage circuits or devices). The processor circuit 106 can be coupled to a high-speed DAC 102, such as include one or more output channels, such as a first channel 124A, or a second channel 124B.

In an example, the system 100 can include a frequency reference 104, such as configured to provide a stabilized reference frequency for use by one or more other portions of the system 100. In an example, the system 100 can include a first mixer 122A, such as configured upconvert a chirped waveform using a specified upconversion LO frequency. The chirped waveform can be provided by the high-speed DAC 102. The upconversion LO frequency can be provided by an oscillator 112. In an example, the first mixer 122A can be configured to provide an upconverted chirped waveform to a frequency multiplier 114A, and the frequency multiplier 114A can output a chirped excitation signal within a specified frequency range for use in exciting a sample 116.

In an example, the system 100 can include a second mixer 118, such as configured to receive an emission from the sample 116, and to downconvert the received emission using a signal based on a specified downconversion LO signal. The downconverted emission signal can be provided to input of an ADC 120, within the available bandwidth of the ADC 120. The processor circuit 106 can be configured to estimate a spectrum of the emission signal using information obtained via the ADC 120.

The specified downconversion LO signal can be provided by the high-speed DAC 102, using one or more of the first or second channels 124A or 124B. The specified downconversion LO signal can be upconverted using the first mixer 122A or a third mixer 122B. The upconverted LO signal can then be frequency multiplied using the first frequency multiplier 114A or a second frequency multiplier 114B, such as to provide the signal based on the specified downconversion LO signal for use by the second mixer 118. In this manner, the high-speed DAC 102 can generate a rapidly-tunable LO signal that can then be routed through the mixer and multiplier chain for use in downconverting the received emissions from the sample 116 using the second mixer 118. In one approach, the mixer and multiplier chain can be independent of the chain used for the chirped-pulse excitation signal, such as shown by the dotted lines in FIG. 1, and in the illustrative example of FIG. 2A.

Figure 2A:
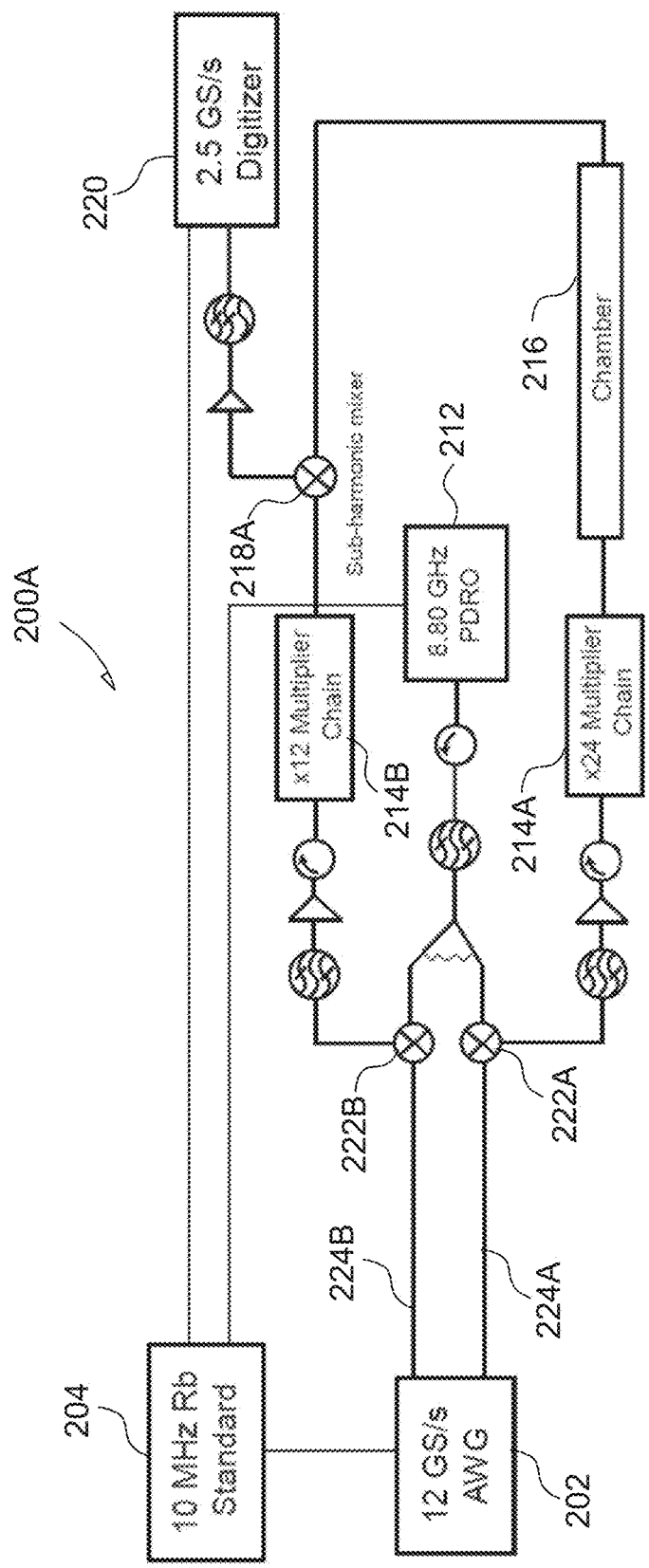
FIG. 2A illustrates generally an illustrative example of a mm-wave spectrometer system, such as including a sub-harmonic mixer having two input ports.
Figure 2B:
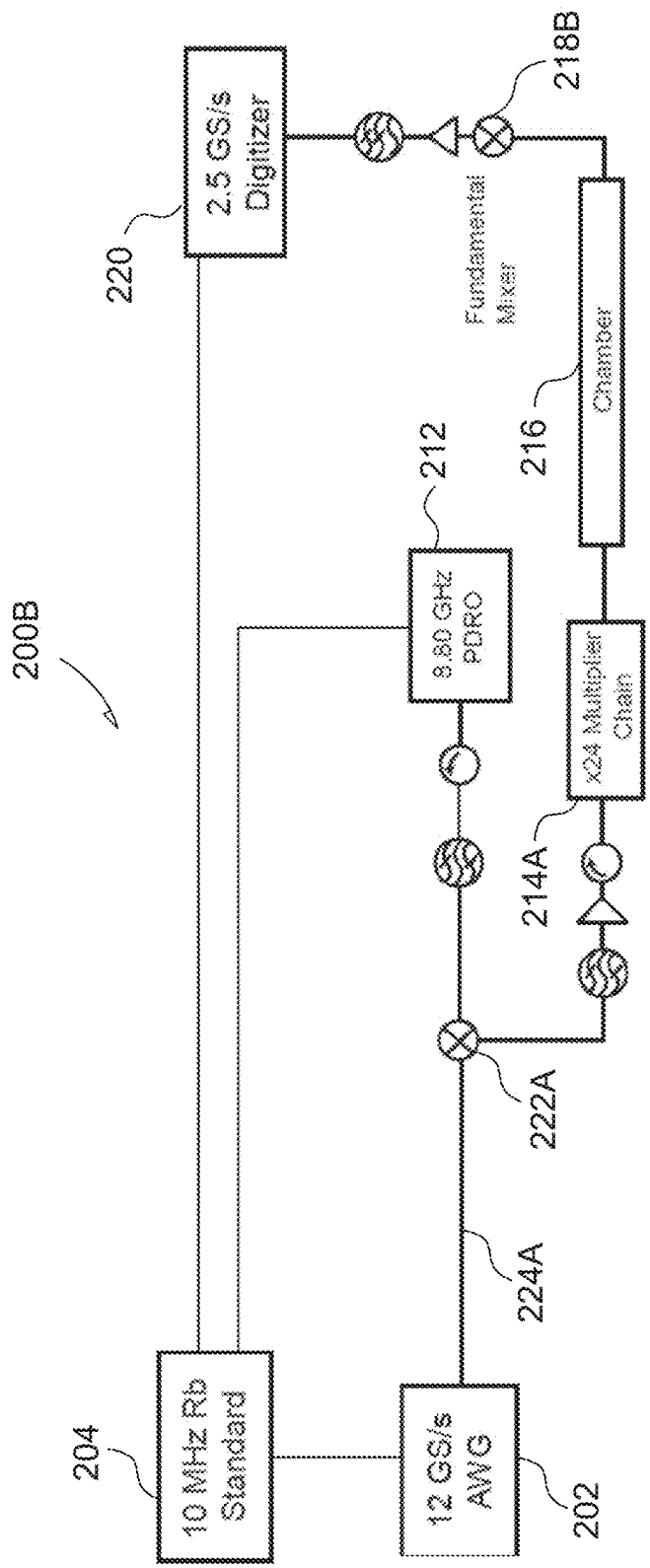
FIG. 2B illustrates generally an illustrative example of a mm-wave spectrometer system, such as including a fundamental-mode mixer having two input ports.

In another approach, the mixer and multiplier used for the downconversion LO signal can be the same as used for excitation of the sample 116, and the path followed by the chirped-excitation pulse can be the same as the path followed by the downconversion LO signal (e.g., the chirped excitation signal delivered to the sample 116 can spatially overlap with the LO signal to be used in downconverting the received emissions), such as if the dotted portions are omitted from FIG. 1, and as shown in the illustrative example of FIG. 2B.

FIG. 2A illustrates generally an illustrative example of a mm-wave spectrometer system 200A, such as operable in a frequency range from about 260 GHz to about 290 GHz, and including a sub-harmonic mixer 218A having two input ports. In this illustrative example, the system 200A can include an AWG 202 having two channels, such as including a first channel 224A that can be used to generate the chirped excitation pulse (e.g., upconverted, frequency multiplied, or amplified before passing through a gaseous sample in a chamber 216), and second channel 224B to provide a specified downconversion LO frequency for use in downconverting the molecular free induction decay (FID) signal to a lower frequency range where it can be digitized by a digitizer 220.

In the example of FIG. 2A, similar to the example of FIG. 1, a first mixer 222A be used to upconvert a chirped waveform prior to multiplication by a 24× multiplier chain 214A. One or more amplifiers, filters, or isolators (e.g., one or more circulators) can be used to further condition the chirped waveform, such as shown in the examples of FIGS. 2A and 2B. In the examples of FIGS. 2A and 2B, an 8.8 GHz phase-locked dielectric resonator oscillator (PDRO) 212 can provide an upconversion LO frequency to one or more of the first mixer 222A or a second mixer 222B.

In the example of FIG. 2A, the second mixer 222B can upconvert the received downconversion LO frequency, such as using the PDRO 212, and the resulting upconverted signal can then be frequency multiplied using a second frequency multiplier chain 214B, such as including a 12× multiplication factor. The sub-harmonic mixer 218 can provide an additional inherent 2× multiplication factor, such as for downconverting received emission from the sample within the chamber 216 into a bandwidth range suitable for the digitizer 220, thus effectively the downconversion LO pathway can provide the same multiplication factor as the 24× multiplier chain 214A.

In an illustrative example, such as to provide the experimentally-obtained information for the examples herein, the AWG 202 can use a sampling rate of about 12 Gs/s (e.g., about 83 picosecond (ps) time resolution). In an example, a single-channel AWG can be used in the sub-harmonic mixer design of FIG. 2A, such as by adding a single-pole double-throw (SPDT) switch to the first channel 224A and directing the chirped pulse and LO signals to their respective multiplier chains, or using a configuration shown in the illustrative example of FIG. 2C.

In the dual-AWG-channel approach shown in the example of FIG. 2A, the downconversion LO signal is generally output prior to the chirped-pulse creation. The present inventors have recognized, among other things, that an advantage of this arrangement is that a chirped excitation pulse generated using the first channel that is transmitted through the sample chamber 216 can be monitored (e.g., with removal of the high-gain preamplifier), such as to assess the quality of the chirped excitation pulse, but at the cost of using the dual-channel approach as compared to single-channel arrangements discussed elsewhere herein.

FIG. 2B illustrates generally an illustrative example of a mm-wave spectrometer system 200B, such as including a fundamental-mode mixer 218B having two input ports. In an example, the fundamental-mode mixer 218B can be used for mm-wave/THz downconversion to a frequency range suitable for the digitizer 220. Generally, the fundamental-mode mixer 218B uses an LO signal path and an excitation signal path that spatially overlap. The physics of chirped-pulse Fourier transform spectroscopy provides that the molecular emission follows the same path as the light from the excitation source. Therefore, the segmented CP-FT measurement can be made by using a single AWG channel that has the chirped pulse during a first duration followed by an LO frequency during a second duration, such as in a single waveform. Such a waveform can be transmitted through the sample and the molecules will emit their free induction decay following chirped-pulse excitation. Such FID emission can then mix with (e.g., beat against) the LO frequency being transmitted through the sample at the fundamental-mode mixer 218B.

Figure 2C:
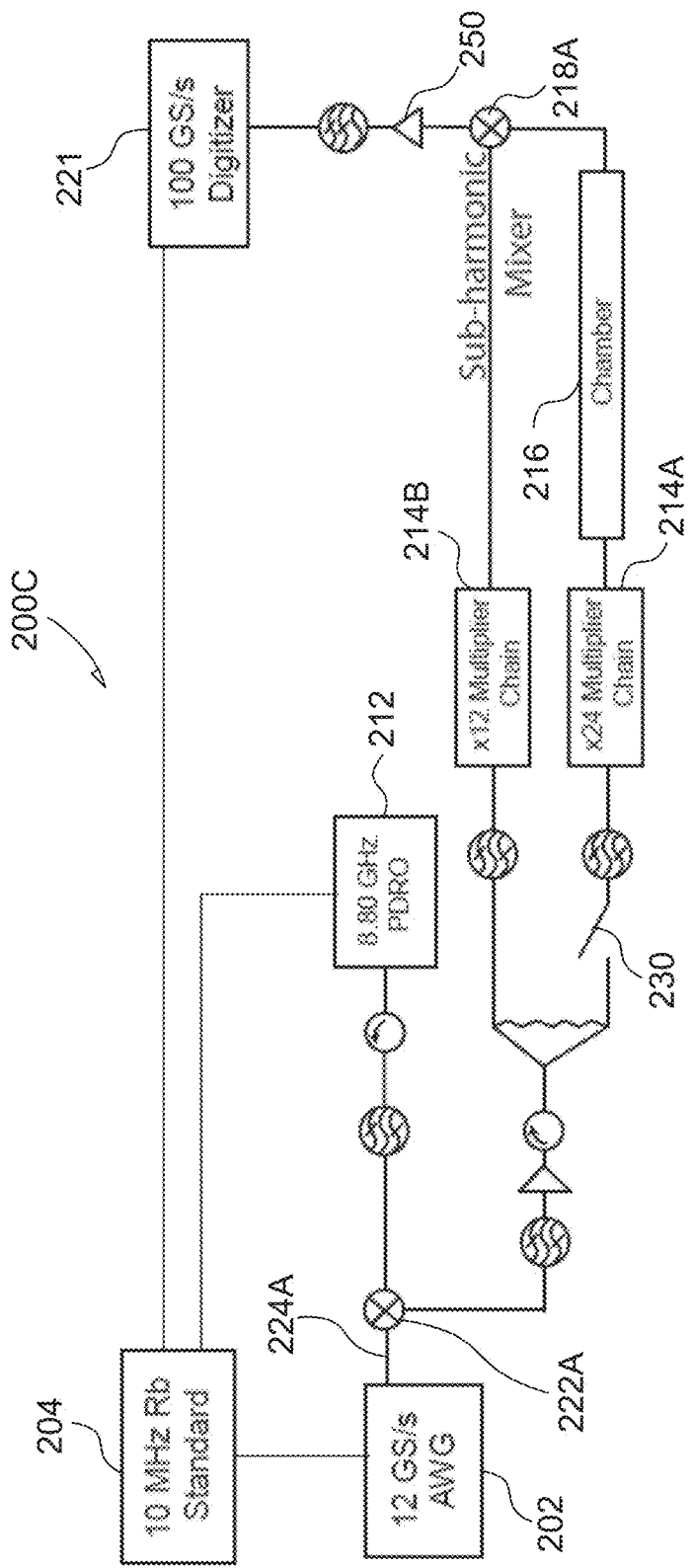
FIG. 2C illustrates generally an illustrative example of a mm-wave spectrometer system, such as including a sub-harmonic mixer and a single-channel arbitrary waveform generator (AWG) implementation.

FIG. 2C illustrates generally an illustrative example of a mm-wave spectrometer system 200C, such as including a sub-harmonic mixer 218A and a switch 230, such as to provide a spectrometer including a single-channel arbitrary waveform generator (AWG) implementation. In contrast to the configuration shown in FIG. 2A, the configuration of FIG. 2C can use a single (e.g., shared) AWG channel 224A to provide both a downconversion LO signal and a chirped excitation pulse.

For example, a first mixer 222A can be coupled to an oscillator (e.g., a PDRO 212 similarly to the examples of FIGS. 2A and 2B), such as for upconversion of both the LO signal generated by the AWG 202, and a chirped excitation pulse generated by the AWG 202. The present inventors have recognized, among other things, that a complexity and cost of the system 200C can be heavily influenced by the number of high-speed AWG channels included in the system. The single AWG channel 224A included in the example of FIG. 2C can help to reduce system complexity and component count, along with a corresponding reduction in cost, without compromising measurement quality (as shown in the illustrative example of FIG. 10).

The system 200C of FIG. 2C can be operated in a manner where the AWG 202 generates a single waveform that includes the chirped excitation pulse followed by a specified single frequency sign wave for use as the downconversion LO signal. For example, such a single frequency sine wave output can be generated immediately or otherwise closely following the chirped excitation pulse. The output of the frequency upconversion provided at the output of the first mixer 222A can be power divided into two signal lines, including a first path for the chirped excitation pulse, including a 24× multiplier chain 214A and the sample chamber 216, and a second path including a 12× multiplier chain 214B to provide the downconversion LO signal to the sub-harmonic mixer 218A. In an example, a switch 230, such as a Transistor-Transistor-Logic (TTL) level driven microwave PIN-diode switch, can be included in the first path to allow a chirped excitation pulse to pass to the sample chamber 216, and suppressing or inhibiting passage of the downconversion LO signal. In this manner, the configuration shown in FIG. 2C allows the downconversion LO signal to bypass the sample chamber. In an example, the trigger or control signal for the switch can be obtained using a marker channel output of the AWG 202.

Generally, excitation and detection are time-separated events in CP-FT spectroscopy, as discussed further elsewhere herein. Accordingly, the receive signal path does not need to be in its proper operating state until the end of a respective chirped excitation pulse. In addition, because the chirped-pulse must pass through the sample cell (e.g., chamber 216), it will generally be time-delayed relative to the LO pulse. This time delay can provide sufficient duration for the LO pulse to be generated and have all transient responses sufficiently dissipate before the receive signal path starts to downconvert the molecular free induction decay (FID). In an illustrative example of experimentally-obtained system performance, the main delay, or dead time, is the recovery of the high gain, low noise IF amplifier 250 from saturation once the chirped excitation pulse ends. Generally, there is no way to protect the receive signal path from the excitation pulse for mm-wave measurements because an extremely high-speed broadband switch would be needed, and placing a switch between the sub-harmonic mixer 218A and IF amplifier 250 would add the switch conversion loss to the overall receiver noise figure while producing transients of its own. Such dead time has been measured to be about 200 ns in experimentally-derived measurements, and generally appears to be longer than any transient settling time of the sub-harmonic mixer 218A.

Figure 10:
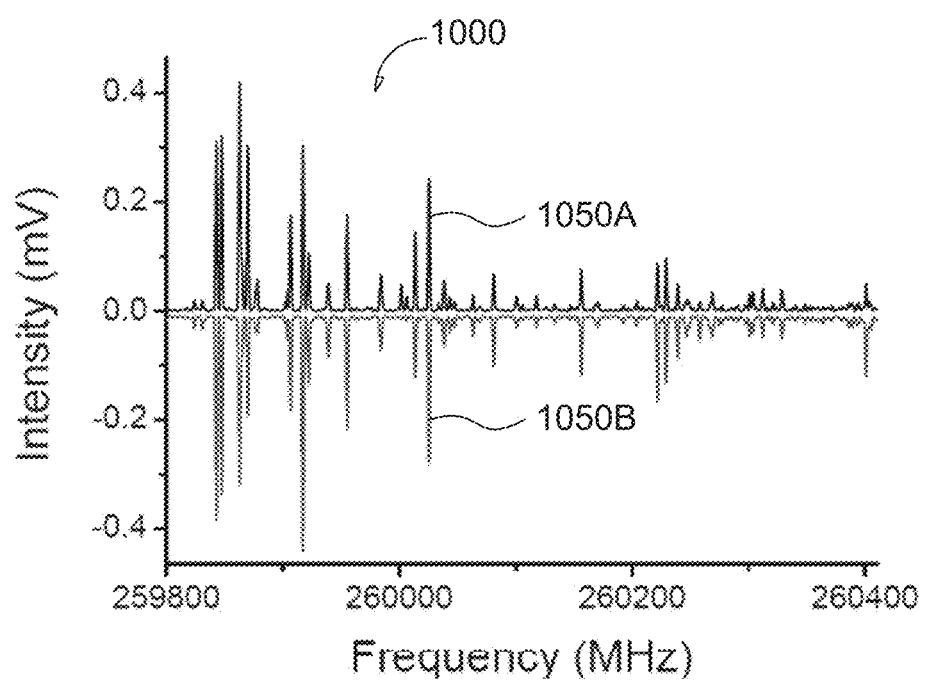
FIG. 10 illustrates generally illustrative examples of experimentally-obtained spectra using a single-channel AWG implementation as compared to a dual-channel AWG implementation.

As shown in FIG. 10, little if any visible difference exists between measurements obtained with a single-channel configuration (e.g., as shown in FIG. 2C), as compared with a dual channel implementation (e.g., as shown in FIG. 2A). The illustrative example of FIG. 2C includes a 100 GS/s digitizer 221. Such a digitizer can be used in relation to other examples, such as shown in FIG. 1, or FIG. 2A or 2B.

FIG. 3A illustrates generally an illustrative example of a spectrogram 300 that can represent respective DAC channel outputs, such as corresponding to a dual-channel example, and FIG. 3B illustrates generally a detailed view of a portion of FIG. 3A. A feature of CP-FT coherent spectroscopy techniques is that the sample excitation and FID downconversion process are separated in time. In FIG. 3B, a first chirped waveform 310A and a specified first LO downconversion frequency 320A can be provided during at least a portion of a first duration 330A (e.g., a first "segment"). In a second "segment," a second chirped waveform 310B and a specified second LO downconversion frequency 320B can be provided during at least a portion of a second duration 330B.

The full available measurement bandwidth of the spectrum (e.g., determined by the bandwidth of the mm-wave/THz multiplier chains or by other system elements) can be segmented for the measurement. In an example, a single pass through the full spectrometer bandwidth can include a series of chirped excitation pulses and a respective downconversion LO frequencies. For example, the LO and chirp frequencies can be increased for each successive segment. For signal averaging in the time domain, the relative phase of the chirped pulse and LO for each segment are reproduced in each pass through the full spectrum. The use of an AWG provides phase reproducibility between sweeps, and provides a capability to switch the LO frequency (with phase lock) on time scales that are short compared to the molecular FID transients.

In an example, in a CP-FT segment, one channel of the arbitrary waveform generator can be used to provide a short-duration linear frequency sweep (e.g., a chirped waveform), which can then be upconverted such using a mixer coupled to a PDRO, and then multiplied after upconversion. Because the chirped waveform only includes a single frequency at any given time, the duration of the pulse is unchanged in the multiplication step but the bandwidth increases. This pulse interacts with a molecular gas sample, and can induce a macroscopic polarization when a rotational transition within the bandwidth of the excitation pulse is crossed. After the chirped pulse, the second AWG channel provides a single-frequency LO pulse that is offset from the sweep range by a small amount (e.g., to limit low-frequency spurious outputs or the effect of 1/f noise). The molecular sample can continue to emit radiation at the frequencies of the molecular transitions in the sweep range, and such radiation can be downconverted with the LO pulse and digitized. Each segment is Fourier transformed, and the segments are pieced together to create a broad-bandwidth spectrum.

In addition to overcoming digitizer bandwidth limitations, the segmented CP-FT approach can be more computationally efficient than determining a spectrum estimate for an entirety of the bandwidth being measured. For example, the number of computations included in a Cooley-Tukey fast Fourier transform technique can scale as $N \log_2 N$, where N can represent the number of data points in the trace. Therefore, a segmented CP-FT spectrum can include fewer computations to Fourier transform a broad bandwidth spectrum than Fourier transforming a single spectrum covering the same total bandwidth.

Figures 4A, 4B:
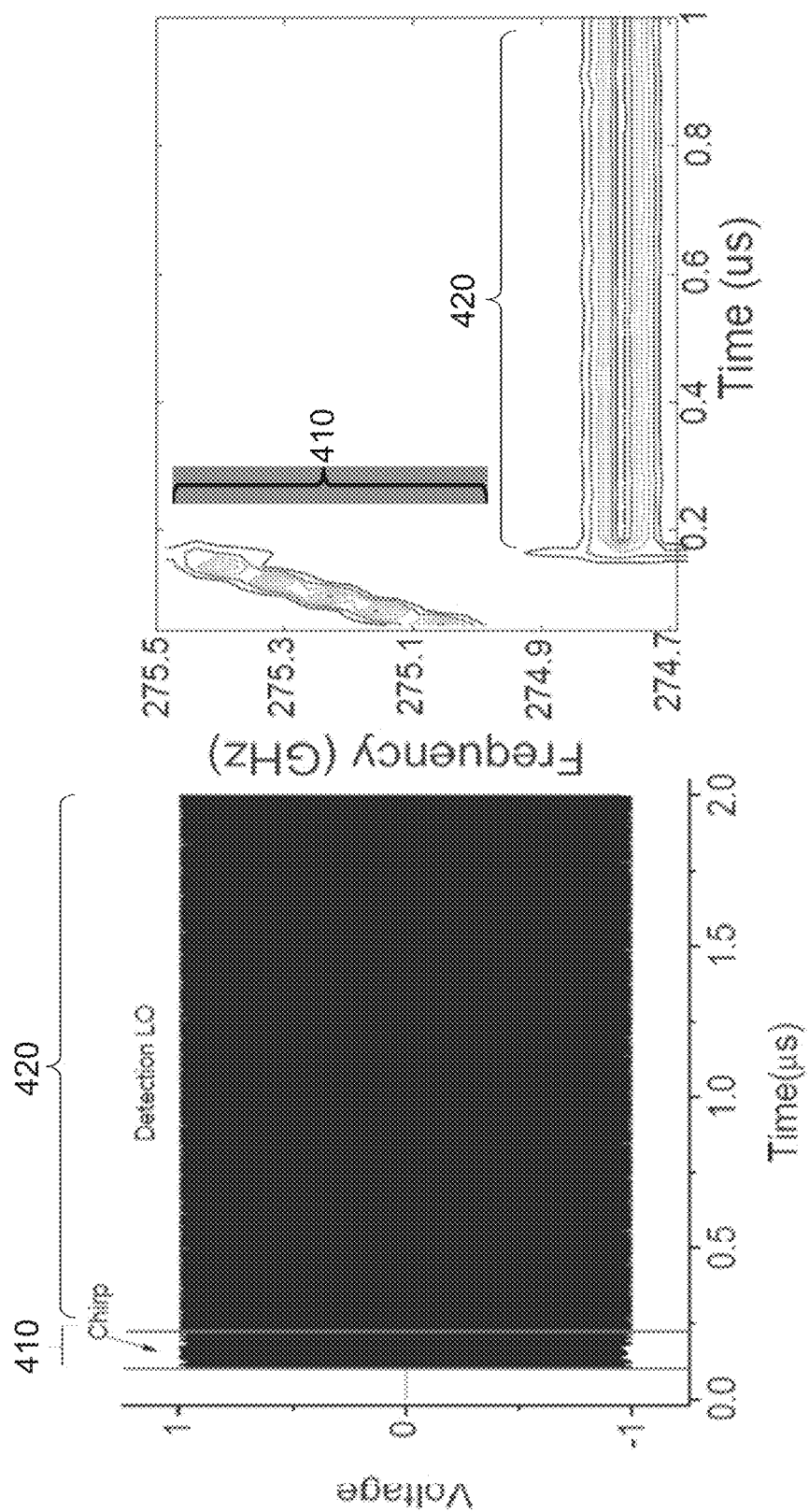
FIG. 4A illustrates generally an illustrative example of a time-domain waveform including a chirped pulse followed by a single-frequency LO pulse.
FIG. 4B illustrates generally a spectrogram of the time-domain waveform of FIG. 4A.

FIG. 4A illustrates generally an illustrative example of a measured time-domain waveform including a chirped pulse followed by a single-frequency LO pulse, and FIG. 4B illustrates generally a spectrogram of the time-domain waveform of FIG. 4A.

In the illustrative examples of FIGS. 4A and 4B, the time domain and spectrogram of a pulse includes a chirped excitation pulse 410 (e.g., about 125 nanoseconds (ns) duration) that can be followed by a single frequency LO pulse 420 (e.g., about 1.875 μs duration). The time-domain pulse of the illustrative example of FIG. 4A was obtained using the system 200A of the example of FIG. 2A. In the illustrative example of FIG. 4B, the spectrogram, which shows only about the first 1 μs of the waveform spectrogram, clearly shows that the AWG-generated waveform includes a rapid chirped excitation pulse 410 followed by a single frequency output for use as the LO pulse 420.

For example, a single AWG channel can be used because the excitation period and detection period are separated in time. Therefore, in an example, the AWG waveform in a respective measurement segment can include the chirped pulse 410, such as followed immediately by the single frequency LO waveform 420. Immediate switching between chirped excitation and single-frequency LO output modes is supported by the AWG. In a fundamental-mode mixer example, such as shown in FIG. 2B, the LO output is directed through the sample. In a sub-harmonic mixer example, a SPDT switch external to the AWG can be used to direct the chirped excitation pulse and the LO pulse for FID downconversion to respective multiplier chains, or a SPST switch external to the AWG can be used to isolate the multiplier chain and sample cell during generation or the LO pulse for downconversion.

Figure 5:
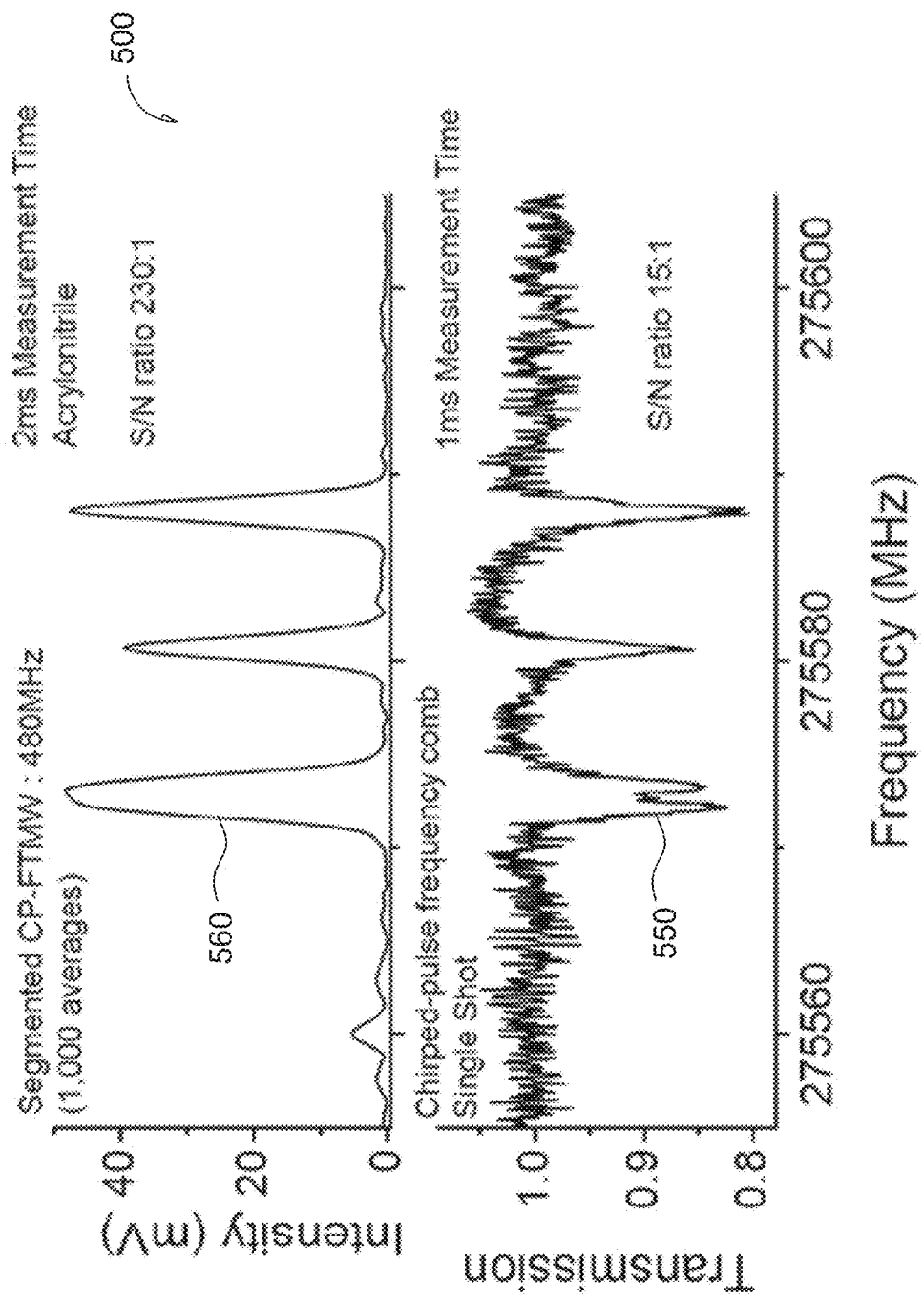
FIG. 5 illustrates generally an illustrative example of a comparison between a direct-absorption spectroscopy technique using a broadband chirped-pulse frequency comb (CP-FC) spectrometer, and a segmented CP-FT approach.

FIG. 5 illustrates generally an illustrative example 500 of a comparison between a transmission spectrum 550 experimentally obtained via direct-absorption spectroscopy technique using a broadband chirped-pulse frequency comb (CP-FC) spectrometer, and an emission spectrum 560 experimentally obtained via segmented CP-FT approach.

Unlike absorption spectroscopy techniques, in a CP-FT approach, background calibration can be performed without a reference cell or sample evacuation.

Because the AWG output is generally not as pure in frequency as a phase-locked oscillator or synthesizer, spurious outputs can occur. In an example, to subtract these effects, a background trace can be collected before the chirped excitation pulse is delivered. For example, the molecular FID signals only occur after excitation by a chirped pulse, so the background trace can be collected in the presence of the gas sample, such as without requiring a reference cell. In experimentally-obtained samples, up to near 550 GHz, such background calibration was not necessary.

In one approach, a chirped-pulse frequency comb (CP-FC) technique can offer similar measurement speed, detection bandwidth, and frequency accuracy in comparison to the segmented CP-FT technique. However, in contrast to CP-FT, CP-FC spectroscopy is an absorption technique, so molecular signals are measured as depletions in the background pulse. As discussed above, for both microwave and infrared techniques, molecular FID emissions, which can be measured against much lower backgrounds, are generally more sensitive techniques for molecular spectroscopy.

In the illustrative example of FIG. 5, a rotational spectrum of vinyl cyanide (acrylonitrile, $CH_2=CHCN$) is shown. The sample pressure was 5 milliTorr (mTorr) with a 4 meter (m) path length. The spectra shown in FIG. 5 shows a portion of the full available 260-290 GHz measurement range. For equal measurement times (e.g., about 2 ms for the CP-FT and about 1 ms for the CP-FC—where the CP-FC measurement also included an additional 1 ms measurement of the background), the sensitivity in CP-FT can be about a factor of 10 higher (e.g., a signal-to-noise ratio (S/N) can be about 230:1 for the segmented CP-FT technique as compared to about 15:1 for the CP-FC technique).

Figure 6A:
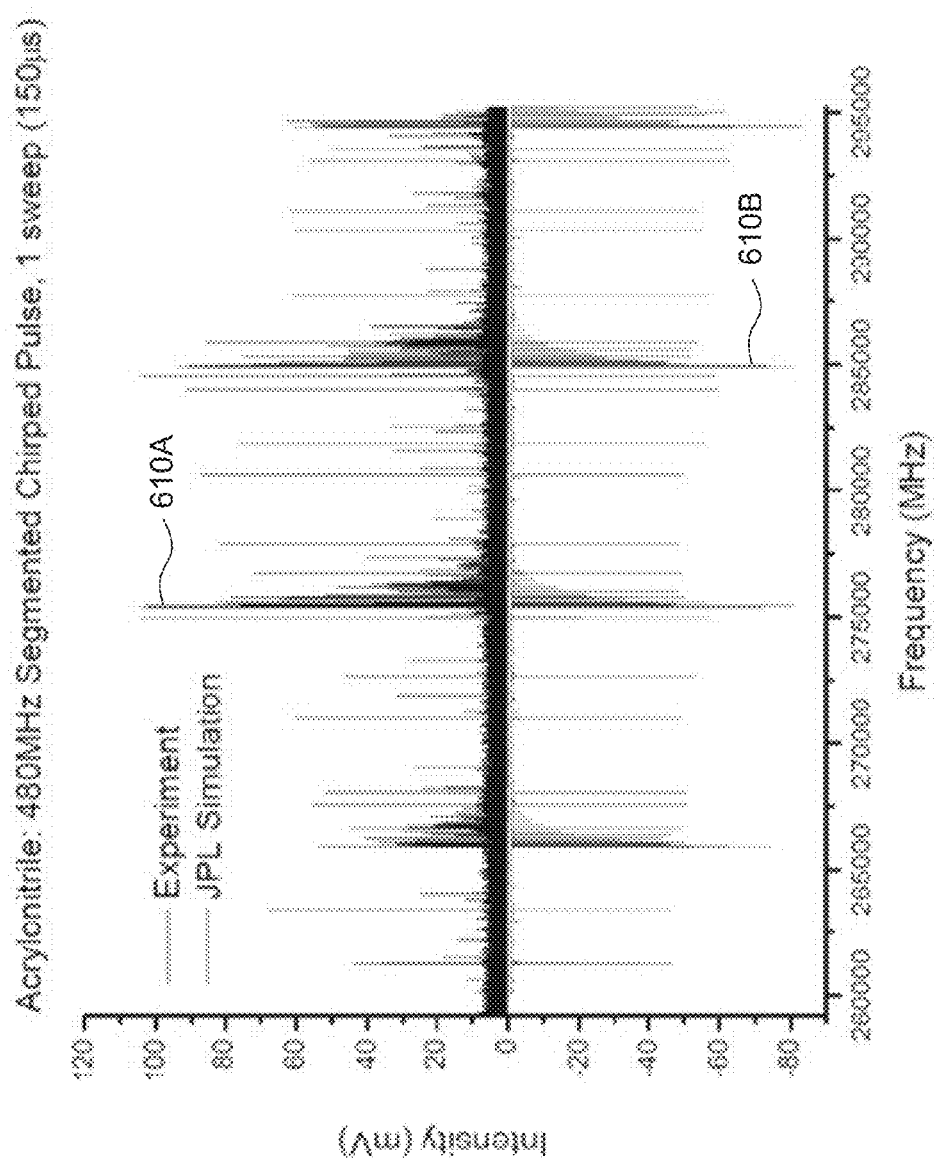
FIGS. 6A through 6B illustrate generally an illustrative example of an experimentally-obtained spectrum for vinyl cyanide from 260 GHz to 290 GHz, using a segmented CP-FT approach, as compared to a simulated spectrum.
Figure 6B:
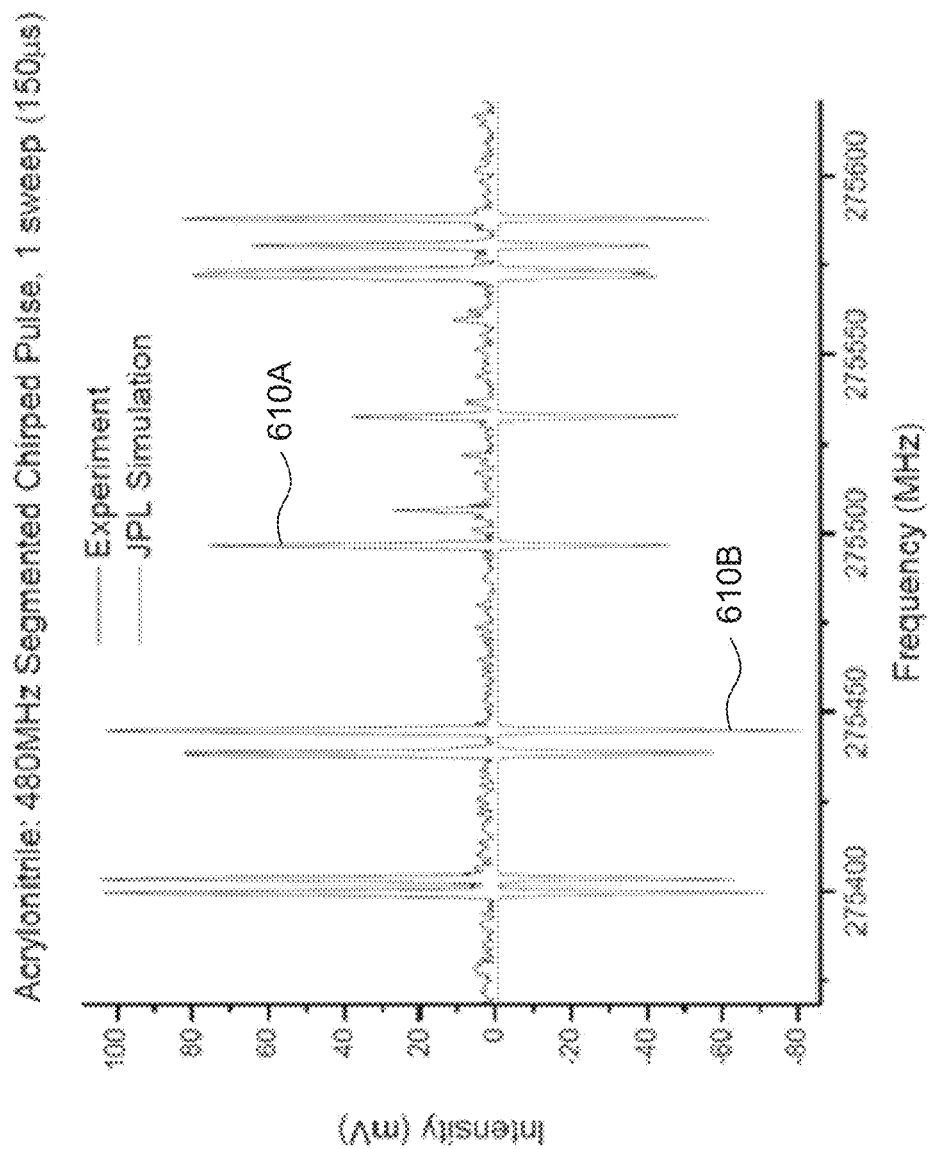

FIGS. 6A through 6B illustrate generally an illustrative example of an experimentally-obtained spectrum for vinyl cyanide from 260 GHz to 290 GHz, using a segmented CP-FT approach, as compared to a simulated spectrum. In FIGS. 6A and 6B, a measured spectrum 610A can be compared to a simulated spectrum 610B, the simulated spectrum 610B provided using information from the NASA Jet Propulsion Laboratory (JPL) database. The experimentally-obtained spectrum 610A was acquired using segments corresponding to chirped excitation pulses having about 480 MHz bandwidth, and the downconversion LO was offset by 240 MHz from the excitation bandwidth. The chirped pulse duration was 125 ns and the peak power of the mm-wave excitation pulse was 1 milliwatt (mW). The FID was digitized starting at 40 ns after the end of the excitation pulse (e.g., to allow the receiver to recover from saturation by the excitation pulse) and the FID was collected over a duration of 1.835 µs. The total time for each segment was 2 µs. There were 75 segments in the full spectrum for a total spectrum acquisition time of 150 µs. The sample pressure was about 5 mTorr and the path length was 4 m.

Figure 7A:
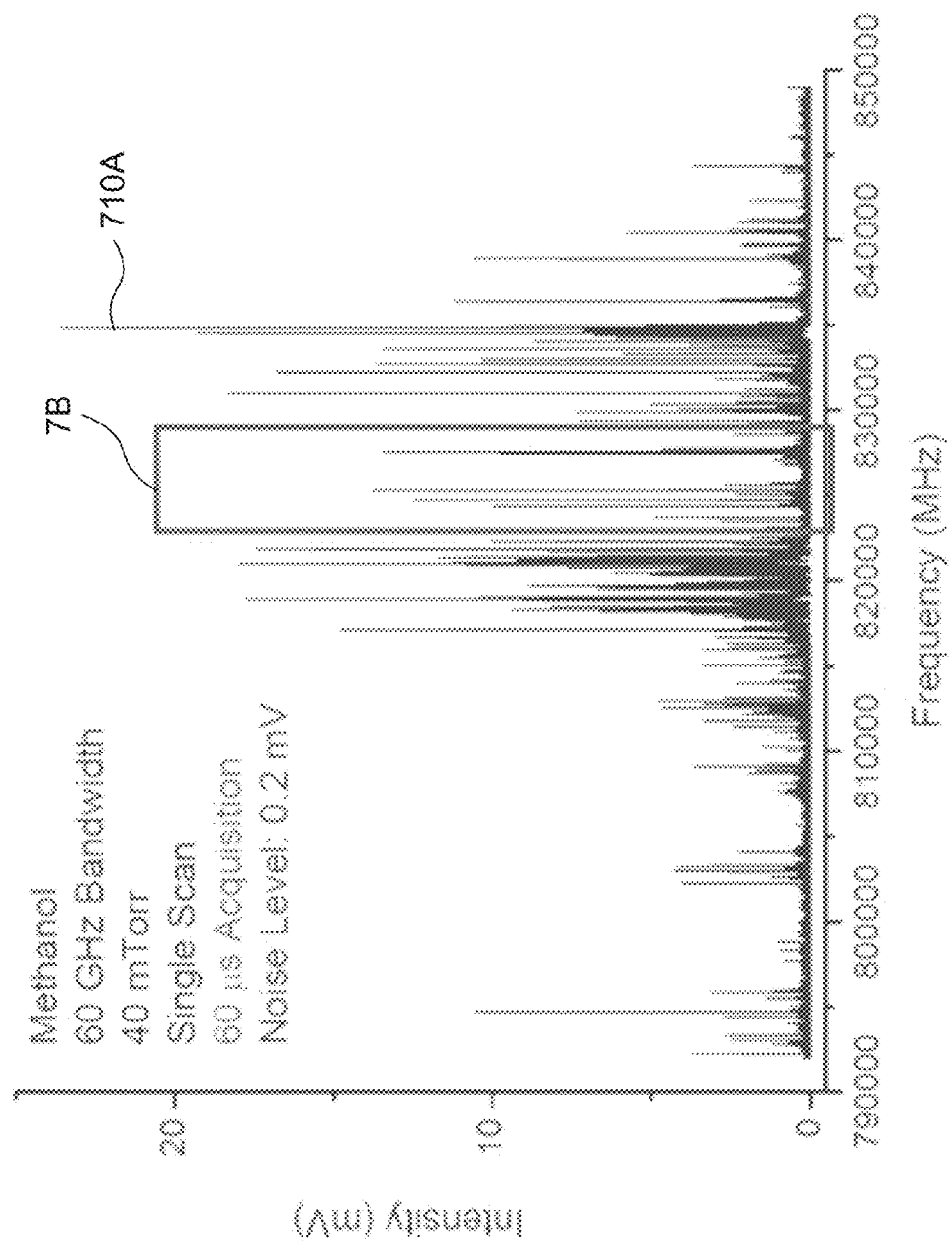
FIGS. 7A through 7B illustrate generally an illustrative example of an experimentally-obtained spectrum for methanol from 0.790 THz to 0.850 THz, using a segmented CP-FT approach, as compared to a simulated spectrum.
Figure 7B:
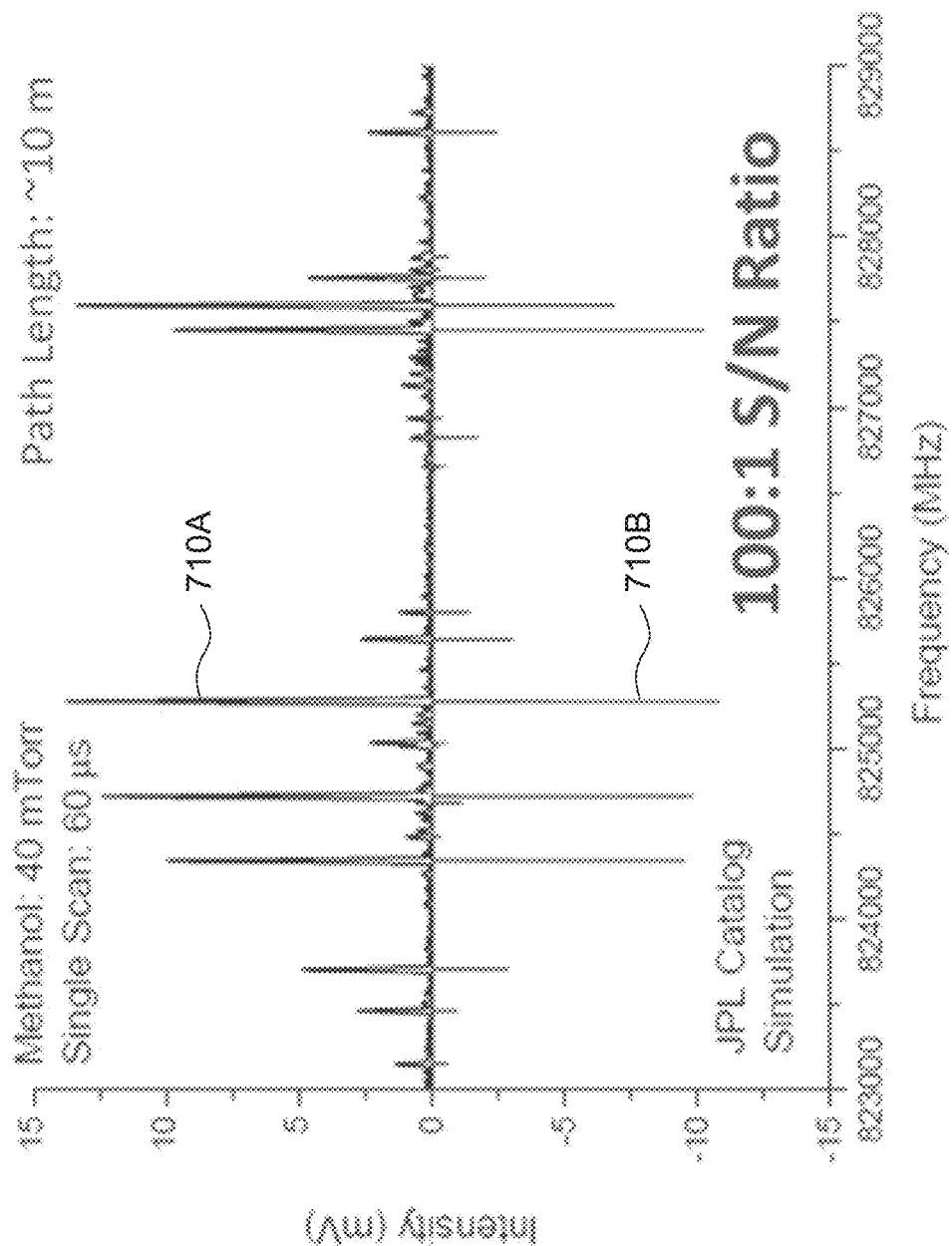

FIGS. 7A through 7B illustrate generally an illustrative example of an experimentally-obtained spectrum 710A for methanol from 0.790 THz to 0.850 THz, using a segmented CP-FT approach, as compared to a simulated spectrum.

The frequency range of the example of FIGS. 7A and 7B was made available by adding an additional frequency tripler to the LO and chirped pulse excitation multiplier chains, using a configuration similar to the illustrative example of FIG. 2A. In this illustrative methanol measurement example, the chirped waveform bandwidth corresponding to each segment was also about 500 MHz. However, the faster dephasing (e.g., from Doppler broadening) at higher frequency (and lower sample mass) allowed reduction of the segment time duration to 500 ns. Approximately 60 GHz of spectrum was acquired using 120 segments and a total measurement time of 60 µs. The sample pressure was 40 mTorr and the path length about 10 m. In the illustrative example of FIG. 7B, a portion of the spectrum 710A is compared to a simulated spectrum 710B obtained using information from the NASA JPL catalog.

Figure 8:
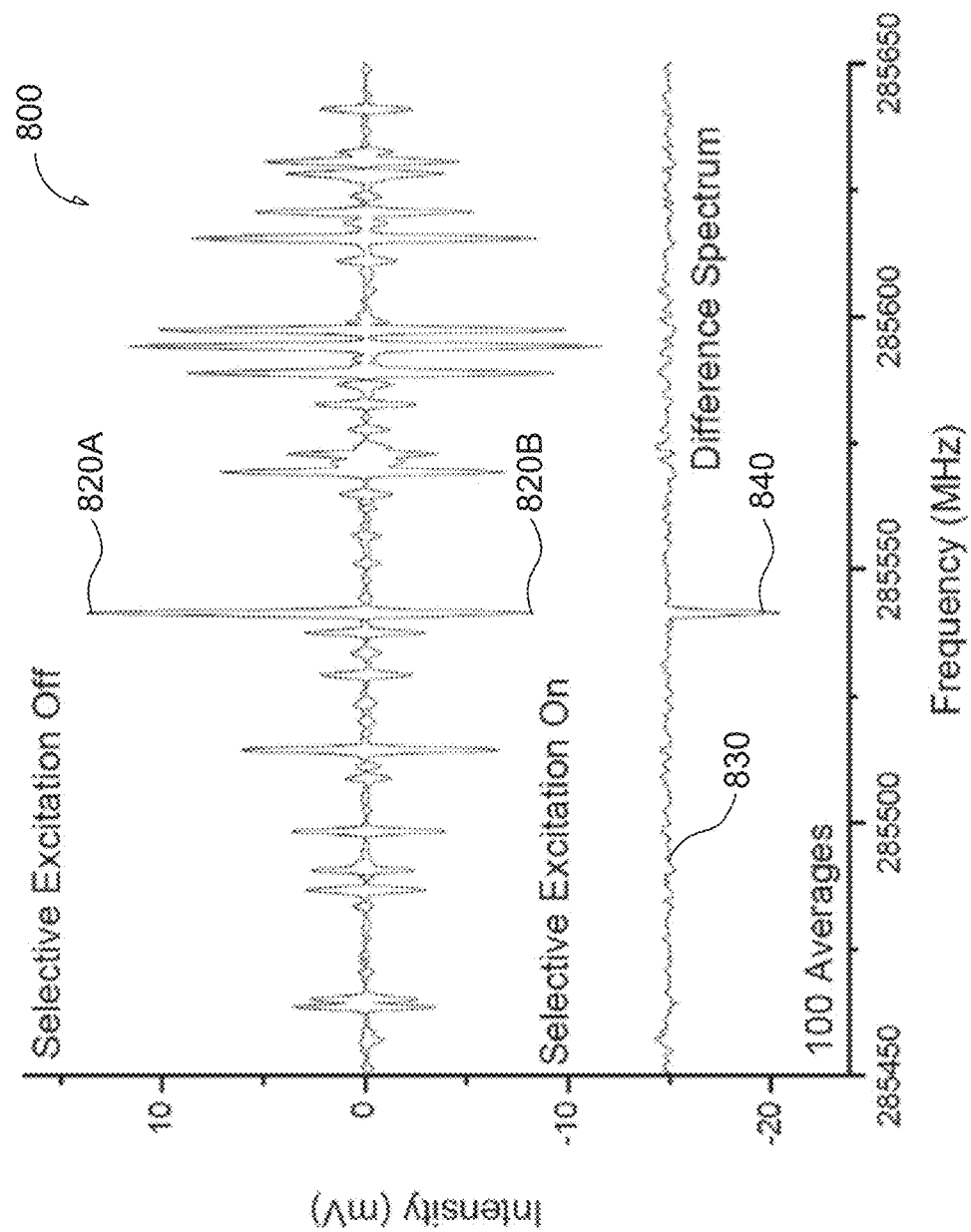
FIG. 8 illustrates generally illustrative examples of experimentally-obtained spectra using a segmented CP-FT approach, and including a double-resonance measurement technique.

FIG. 8 illustrates generally an illustrative example 800 of experimentally-obtained spectra using a segmented CP-FT approach, and including a double-resonance measurement technique. As a coherent spectroscopy, the CP-FT method permits double-resonance measurements that can produce high signal modulation. Double-resonance spectroscopy can be a useful technique for identifying an unknown spectrum by showing the "connectivity" of the rotational spectroscopy transitions. Such connectivity occurs when transitions share a common quantum state. Such techniques can be especially useful when the measured spectrum comes from a complex mixture of different species.

In an example, a double-resonance measurement can include using three waveforms that can be separate in time and, for example, generated by a single AWG channel. In an illustrative example, two excitation pulses that interact with the molecular sample can be generated using one AWG channel, and the LO can be generated using a second AWG channel, such as in a sub-harmonic mixer design (e.g., as shown in the illustrative example of FIG. 2A).

In an example, the excitation pulses include first a chirped pulse that excites a segment of the rotational spectrum and coherently excited the sample, and a second pulse following the chirped-pulse, the second pulse comprising a single fixed frequency excitation. In an example, the frequency of the second pulse is selected to be coincident with a transition in the spectrum. The effect of this frequency-selective pulse can be to destroy the coherence for any transition that shares a quantum state with the selected "pumped" transition.

This causes a detectable reduction in the intensity of any transitions excited by the chirped pulse that are in "double-resonance." The illustrative example of FIG. 8 includes a double-resonance measurement for the vinyl cyanide (acrylonitrile) spectrum of FIGS. 6A and 6B. In this illustrative example, a chirped excitation pulse can polarize the sample in the frequency segment of 285.360-285.840 GHz. As discussed in relation to FIG. 6A, a first spectrum can be experimentally obtained, such as including a rotational transition 820A that has been previously analyzed and "assigned" as $30_{4,26}$-$29_{4,25}$ (e.g., a standard asymmetric top quantum level designation of molecular spectroscopy: $J_{Ka,Kc}$).

The frequency for this transition is 285.5926 GHz. The selective excitation pulse included a frequency of 275.9974 GHz and is resonant with the previously assigned $29_{4,25}$-$28_{4,24}$ transition. Because these two transitions share a quantum level ($29_{4,25}$), the selective excitation pulse reduces the signal intensity of the monitored $30_{4,26}$-$29_{4,25}$ transition (by about 50%), at 820B, without affecting nearby transitions not in double-resonance. The performance of the selective excitation double-resonance scheme is highlighted by displaying a difference spectrum 830 at the bottom of the figure, showing a prominent dip 840 corresponding to the $30_{4,26}$-$29_{4,25}$ transition 820A at 285.5926 GHz.

In an example, double resonance spectroscopy can be used such as to create a 2-D spectrum showing all the pairs of transitions that share a quantum state in the spectrum, such as similar to techniques that can be used for 2-D nuclear magnetic resonance (NMR) spectroscopy. Because of the large number of individual measurements performed in the segmented CP-FT technique, a new double resonance measurement can be performed in every segment, allowing for faster determination of the 2-D spectrum, and allowing for more rapid interpretation of complex unknown spectra.

Figure 9:
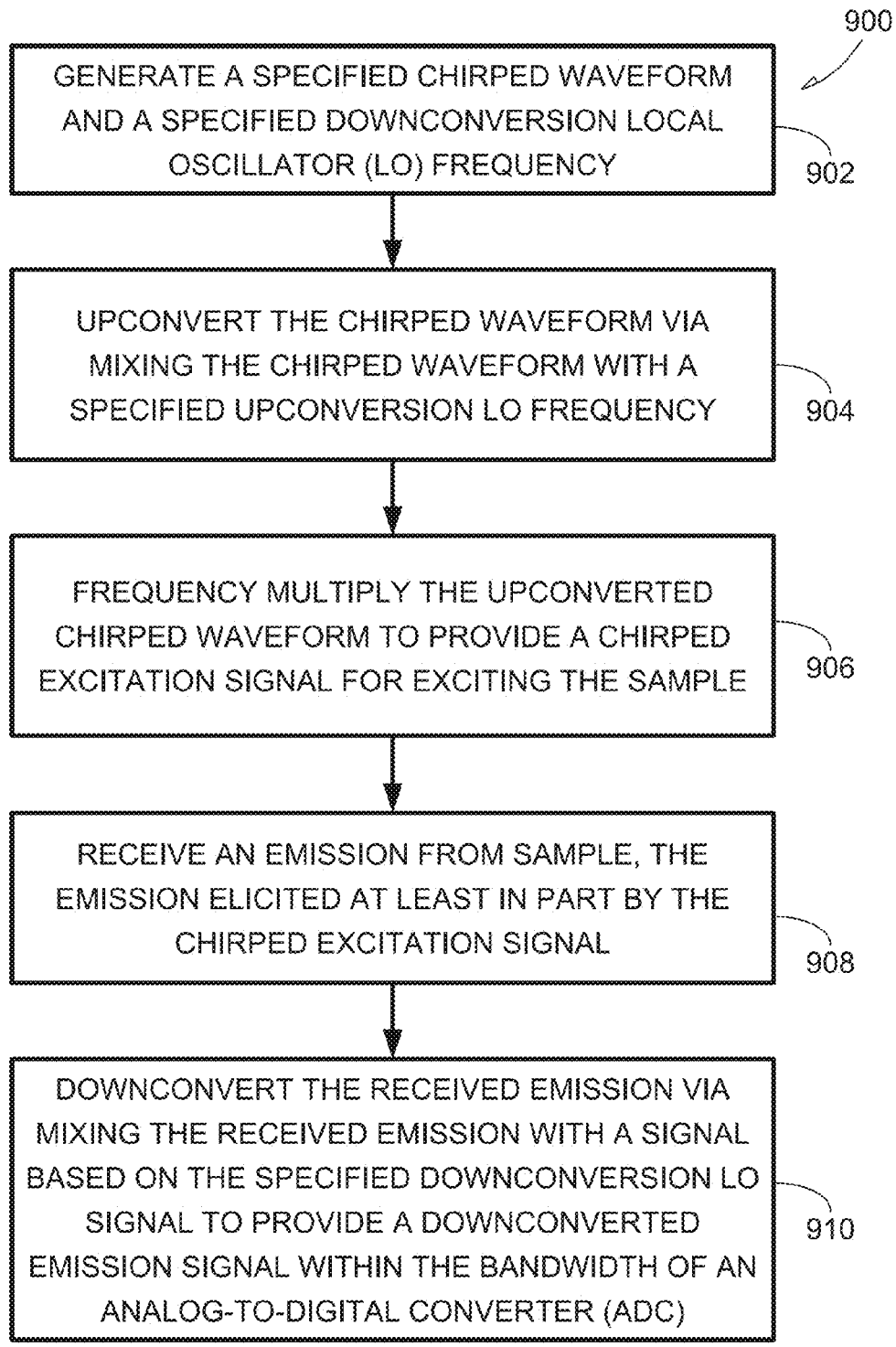
FIG. 9 illustrates generally a technique, such as a method for obtaining an emission from a sample in response to excitation using a specified range of excitation frequencies.

FIG. 9 illustrates generally a technique 900, such as a method for obtaining an emission from a sample in response to excitation using a specified range of excitation frequencies. The technique 900 can include using one or more portions of the apparatus of the examples of FIG. 1, 2A, or 2B.

At 902, a specified chirped waveform and a specified downconversion LO frequency can be generated, such as using a high-speed DAC (e.g., an AWG or one or more other circuits or systems). At 904, the chirped waveform can be upconverted, such as via mixing the chirped waveform with a specified upconversion LO frequency. At 906, the upconverted chirped waveform can be frequency multiplied to provide a chirped excitation signal for exciting the sample.

At 908, an emission can be received from the sample, the emission elicited at least in part by the chirped excitation signal. At 910, the received emission can be downconverted, such as by mixing the received emission with a signal based on the specified downconversion LO signal to provide a downconverted emission signal within the bandwidth of an ADC converter. In an example, the technique can include a segmented CP-FT technique, such as including generating a first specified chirped waveform during a first duration, and a second chirped waveform during a second duration, the first and second chirped waveforms including respective bandwidths specified based at least in part on the bandwidth of the ADC and including a total bandwidth corresponding to the specified range of excitation frequencies.

FIG. 10 illustrates generally illustrative examples of experimentally-obtained spectra using a single-channel AWG implementation as compared to a dual-channel AWG implementation. The single-channel AWG implementation corresponds to the system shown in the illustrative example of FIG. 2C, which was used to provide a first spectrum 1050A, and the dual-channel AWG implementation corresponds to the system shown in the illustrative example of FIG. 2A, which was used to provide the second spectrum 1050B, but with a 100 GS/s digitizer provided as the analog-to-digital converter (ADC). The molecular sample used for experimentally obtaining the first and second spectra 1050A and 1050B was ethyl cyanide at 0.5 mT pressure. As shown in FIG. 10, no significant difference in the obtained spectra 1050A and 1050B is visible.

In an illustrative example, the CP-FT techniques and apparatus described herein can be used to obtain high-sensitivity spectra across large bandwidths (e.g., up to about 100 GHz or more), with an acquisition time that can be about 1 ms or less. In an illustrative example, a relatively low digitizer detection bandwidth (e.g., less than about 1 GHz) can be used. Generally, using the CP-FT techniques described herein, the received signals can be coherently detected in the time domain, so signal averaging (or determination of one or more other central tendencies) can be performed, such as to enhance sensitivity as desired for a specific application.

Because the molecular signals can be digitized in the radio-frequency region of frequencies (rather than the mm-wave range), and the local oscillator sources are referenced to a high-precision (e.g., rubidium) frequency standard, the absolute frequency accuracy of the segmented CP-FT technique can be extremely high, such as limited only by the uncertainty in the molecular line width, and no calibrant is necessary. In contrast to CP-FT approaches, some other approaches require calibration such as using spectral lines of known frequency, or use of etalons, such as to correct for a nonlinearity of a frequency sweeping source on every scan.

VARIOUS NOTES & EXAMPLES

Example 1 can include subject matter (such as an apparatus, a method, a means for performing acts, or a machine readable medium including instructions that, when performed by the machine, that can cause the machine to perform acts), such as can include a method for obtaining an emission from a sample in response to excitation using a specified range of excitation frequencies, the method comprising generating a specified chirped waveform and a specified downconversion local oscillator (LO) frequency using a digital-to-analog converter (DAC), upconverting the chirped waveform via mixing the chirped waveform with a specified upconversion LO frequency, frequency multiplying the upconverted chirped waveform to provide a chirped excitation signal for exciting the sample, receiving an emission from the sample, the emission elicited at least in part by the chirped excitation signal, downconverting the received emission via mixing the received emission with a signal based on the specified downconversion LO signal to provide a downconverted emission signal within the bandwidth of an analog-to-digital converter (ADC). In Example 1, the generating the specified chirped waveform can include generating a first chirped waveform during a first duration, and a second chirped waveform during a second duration, the first and second chirped waveforms including respective bandwidths specified based at least in part on the bandwidth of the ADC and including a total bandwidth corresponding to the specified range of excitation frequencies.

Example 2 can include, or can optionally be combined with the subject matter of Example 1, to optionally include estimating a first spectrum corresponding to the specified range of excitation frequencies, including using information corresponding to respective emissions obtained during at least a portion of the first and second durations.

Example 3 can include, or can optionally be combined with the subject matter of one or any combination of Examples 1 or 2 to optionally include generating a specified fixed frequency to excite the sample after generating the chirped excitation signal, and estimating a second spectrum using information corresponding to an emission obtained from the sample in response to the chirped excitation signal and in response to the specified fixed frequency.

Example 4 can include, or can optionally be combined with the subject matter Example 3 to optionally include a specified fixed frequency that modulates an energy level transition of the sample after the sample is coherently excited using the chirped excitation signal.

Example 5 can include, or can optionally be combined with the subject matter of one or any combination of Examples 3 or 4 to optionally include D determining a relative indication of information using the estimated first and second spectra.

Example 6 can include, or can optionally be combined with the subject matter of one or any combination of Examples 1 through 5 to optionally include receiving respective first and second downconverted received emissions obtained via repeating the chirped excitation of the sample, and determining a central tendency of information obtained from the first and second downconverted received emissions.

Example 7 can include, or can optionally be combined with the subject matter of one or any combination of Examples 1 through 6 to optionally include receiving an emission comprising a free-induction decay emission from a sample comprising a gaseous species.

Example 8 can include, or can optionally be combined with the subject matter of one or any combination of Examples 1 through 7 to optionally include generating the specified chirped waveform includes using a first channel of an arbitrary waveform generator (AWG), the generating the specified downconversion LO frequency including using a second channel of an AWG, and the downconverting the emission signal including using a sub-harmonic mixer comprising a first port configured to receive the signal based on the specified downconversion LO frequency, a second port configured to receive the emission; and a third port configured to provide the downconverted emission signal within the bandwidth of the ADC.

Example 9 can include, or can optionally be combined with the subject matter of one or any combination of Examples 1 through 7 to optionally include E upconverting the specified downconversion LO frequency and frequency multiplying the upconverted output to provide the signal based on the downconversion LO frequency, the downconverting the emission including using a fundamental mode mixer comprising a single input port configured to receive the signal based on the downconversion LO frequency and the emission, and a second port configured to provide the downconverted emission signal, the signal based on the LO frequency propagating via the same spatial path as the chirped excitation signal and the elicited emission.

Example 10 can include, or can optionally be combined with the subject matter of one or any combination of Examples 1 through 9 to optionally include a frequency reference comprising a precision oscillator configured to provide a reference frequency based at least in part on an atomic or molecular energy level transition.

Example 11 can include, or can optionally be combined with the subject matter of one or any combination of Examples 1-10 to include, subject matter (such as an apparatus, a method, a means for performing acts, or a machine readable medium including instructions that, when performed by the machine, that can cause the machine to perform acts), such as can include a digital-to-analog converter (DAC) coupled to a frequency reference and configured to provide a specified chirped waveform and a specified downconversion local oscillator (LO) frequency, a phase-locked oscillator coupled to the frequency reference and configured to provide a specified upconversion LO frequency, a first mixer configured to receive the specified chirp waveform from the DAC and the specified upconversion LO frequency from the phase-locked oscillator, and configured to provide an upconverted chirped waveform, a frequency multiplier configured to receive the upconverted chirped waveform and configured to provide a chirped excitation signal for exciting a sample, and a second mixer configured to receive an emission from the sample, the emission elicited at least in part by the chirped excitation signal, the second mixer configured to receive the specified downconversion LO frequency from the DAC, and configured to provide an output signal within the bandwidth of an analog-to-digital converter. In Example 11, the DAC can be configured to generate a first specified chirped waveform during a first duration, and a second chirped waveform during a second duration, the first and second chirped waveforms including respective bandwidths specified based at least in part on the bandwidth of the ADC and including a total bandwidth corresponding to the specified range of excitation frequencies.

Example 12 can include, or can optionally be combined with the subject matter of Example 11, to optionally include an ADC coupled to the second mixer, and a processor coupled to the ADC, the processor configured to estimate a first spectrum corresponding to the specified range of excitation frequencies, including using information corresponding to respective emissions obtained during at least a portion of the first and second durations.

Example 13 can include, or can optionally be combined with the subject matter of Example 12, to optionally include a DAC configured to generate a specified fixed frequency to excite the sample after generating the chirped excitation signal, and a processor configured to estimate a second spectrum using information corresponding to an emission obtained from the sample in response to the chirped excitation signal and in response to the specified fixed frequency.

Example 14 can include, or can optionally be combined with the subject matter of one or any combination of Examples 11 through 13 to optionally include an emission comprising a free-induction decay emission from a sample comprising a gaseous species.

Example 15 can include, or can optionally be combined with the subject matter of one or any combination of Examples 11 through 14 to optionally include an arbitrary waveform generator (AWG) including the DAC, the AWG configured to generate the specified chirped waveform using a first channel of the AWG, and configured to generate the specified downconversion LO frequency using the second channel of the AWG, and a second mixer comprising a sub-harmonic mixer including a first port configured to receive the signal based on the specified downconversion LO frequency, a second port configured to receive the emission; and a third port configured to provide the downconverted emission signal within the bandwidth of the ADC.

Example 16 can include, or can optionally be combined with the subject matter of one or any combination of Examples 11 through 14 to optionally include a third mixer configured to upconvert the specified downconversion LO frequency to provide an upconverted output, and a second frequency multiplier configured to frequency multiply the upconverted output to provide the signal based on the downconversion LO frequency, the second mixer comprising a fundamental mode mixer including a single input port configured to receive the signal based on the downconversion LO frequency and the emission, and a second port configured to provide the downconverted emission signal, and the signal based on the LO frequency propagating via the same spatial path as the chirped excitation signal and the elicited emission.

Example 17 can include, or can optionally be combined with the subject matter of one or any combination of Examples 11 through 16 to optionally include a frequency reference including a precision oscillator configured to provide a reference frequency derived at least in part from an atomic or molecular energy level transition.

Example 18 can include, or can optionally be combined with any portion or combination of any portions of any one or more of Examples 1-17 to include, subject matter that can include means for performing any one or more of the functions of Examples 1-20, or a machine-readable medium including instructions that, when performed by a machine, cause the machine to perform any one or more of the functions of Examples 1-20.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A method, comprising:
   receiving a first emission signal from a sample, the first emission signal spanning a first bandwidth and elicited at least in part by a first excitation signal applied to sample;
   mixing the first emission signal with a first local oscillator (LO) to generate a first downconverted emission signal within a conversion bandwidth of an analog-to-digital converter (ADC);
   digitizing the first downconverted emission signal with the ADC to generate a first digital signal;
   receiving a second emission signal from the sample, the second emission signal spanning a second bandwidth different than the first bandwidth and elicited at least in part by a second excitation signal applied to the sample;
   mixing the second emission signal with a second local oscillator (LO) to generate a second downconverted emission signal within the conversion bandwidth of the ADC;
   digitizing the second downconverted emission signal with the ADC to generate a second digital signal; and
   combining the first digital signal and the second digital signal to form a combined digital signal having a bandwidth greater than the conversion bandwidth of the ADC.

2. The method of claim 1, further comprising:
   applying the first excitation signal to the sample, the first excitation signal having a first bandwidth and spanning a first millimeter-wave frequency range, wherein the first emission signal is received in response to the first excitation signal; and
   applying the second excitation signal to the sample, the second excitation signal having a second bandwidth and spanning a second millimeter-wave frequency range different than the first millimeter-wave frequency range, wherein the second emission signal is received in response to the second excitation signal.

3. The method of claim 1, the mixing the first emission signal with the first LO including:
   mixing a first portion of the first emission signal with the first LO at a first frequency; and
   mixing a second portion of the first emission signal with the first LO at a second frequency different from the first frequency.

4. The method of claim 1, the first excitation signal including a first chirped excitation signal and the first LO including a first single-frequency LO.

5. The method of claim 1, the first excitation signal and the first LO having a first relative phase difference and the second excitation signal and the second LO having a second relative phase difference equal to the first relative phase difference.

6. The method of claim 1, herein the first emission signal is representative of a first free-induction decay emission from the sample, and the second emission signal is representative of a second free-induction decay emission from the sample.

7. The method of claim 1, the bandwidth of the combined digital signal being up to 200 GHz.

8. The method of claim 1, the conversion bandwidth of the ADC being about 1 GHz or less.

9. An apparatus, comprising:
a mixer configured to:
mix a first emission signal with a first local oscillator (LO) to generate a first downconverted emission signal, the first emission signal spanning a first band and elicited at least in part by a first excitation signal applied to a sample; and
mix a second emission signal with a second local oscillator (LO) to generate a second downconverted emission signal, the second emission signal spanning a second band different than the first band and elicited at least in part by a second excitation signal applied to the sample;
an analog-to-digital converter (ADC) operably coupled to the mixer and configured to:
digitize the first downconverted emission signal to generate a first digital signal; and
digitize the second downconverted emission signal to generate a second digital signal; and
a processor operably coupled to the ADC and configured to combine the first digital signal and the second digital signal to form a combined digital signal having a bandwidth greater than the conversion bandwidth of the ADC.

10. The apparatus of claim 9, further comprising a signal source configured to:
apply the first excitation signal to the sample, the first excitation signal having a first bandwidth and spanning a first millimeter-wave frequency range, wherein the mixer is configured to receive the first emission signal in response to the first excitation signal,
apply the second excitation signal to the sample, the second excitation signal having a second bandwidth and spanning a second millimeter-wave frequency range different than the first millimeter-wave frequency range, wherein the mixer is configured to receive the second emission signal in response to the second excitation signal.

11. The apparatus of claim 9, the mixer further configured to mix the first emission signal with the first LO by:
mixing a first portion of the first emission signal with the first LO at a first frequency; and
mixing a second portion of the first emission signal with the first LO at a second frequency.

12. The apparatus of claim 9, the first excitation signal including a first chirped excitation signal and the first LO including a first single-frequency LO.

13. The apparatus of claim 9, the first excitation signal and the first LO having a first relative phase difference and the second excitation signal and the second LO having a second relative phase difference equal to the first relative phase difference.

14. The apparatus of claim 9, wherein the first emission signal is representative of a first free-induction decay emission from the sample and the second emission signal is representative of a second free-induction decay emission from the sample.

15. The apparatus of claim 9, further comprising a signal source configured to apply the first excitation signal to the sample, the signal source including:
a digital-to-analog converter (DAC) configured to generate a first chirped waveform; and
a frequency multiplier, operably coupled to the DAC, to generate the first excitation signal from the first chirped waveform.

16. The apparatus of claim 9, further comprising an arbitrary waveform generator (AWG) configured to generate the first excitation signal and the second excitation signal.

17. The apparatus of claim 9, the processor further configured to compute one or more central tendencies associated with the sample based on one or more of the first digital signal, the second digital signal, and the combined digital signal.

18. The apparatus of claim 9, further comprising:
a signal source configured to apply the first excitation signal to the sample and to apply the second excitation signal to the sample; and
a precision oscillator coupled to the signal source and configured to provide a reference frequency based at least in part on an atomic or molecular energy level transition.

19. The apparatus of claim 9, the combined digital signal having a bandwidth of up to 200 GHz.

20. The apparatus of claim 9, wherein the conversion bandwidth of the ADC is about 1 GHz or less.

21. A method, comprising:
digitizing, with an analog-to-digital converter (ADC), a plurality of emission signals to produce a plurality of digital signals, each emission signal in the plurality of emission signals spanning a different bandwidth and representing a different free induction decay by a sample; and
combining the plurality of digital signals to form a combined digital signal having a bandwidth greater than a conversion bandwidth of the ADC.

* * * * *